United States Patent
Collazo et al.

(10) Patent No.: US 10,376,371 B2
(45) Date of Patent: Aug. 13, 2019

(54) STABILIZED KNEE PROSTHESIS

(71) Applicant: Howmedica Osteonics Corp., Mahwah, NJ (US)

(72) Inventors: Carlos E. Collazo, Old Greenwich, CT (US); Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 160 days.

(21) Appl. No.: 15/259,270

(22) Filed: Sep. 8, 2016

(65) Prior Publication Data
US 2016/0374814 A1 Dec. 29, 2016

Related U.S. Application Data

(60) Continuation of application No. 14/027,636, filed on Sep. 16, 2013, now Pat. No. 9,452,051, which is a
(Continued)

(51) Int. Cl.
*A61F 2/38* (2006.01)
*A61F 2/30* (2006.01)

(52) U.S. Cl.
CPC .............. *A61F 2/38* (2013.01); *A61F 2/389* (2013.01); *A61F 2/3836* (2013.01);
(Continued)

(58) Field of Classification Search
CPC ........ A61F 2/38; A61F 2/3836; A61F 2/3859; A61F 2/3886; A61F 2/389
See application file for complete search history.

(56) References Cited

U.S. PATENT DOCUMENTS

| 2,088,724 A | 8/1937 | Rosencrants |
| 3,638,243 A | 2/1972 | Campbell, Jr. et al. |

(Continued)

FOREIGN PATENT DOCUMENTS

| DE | 19962324 A1 | 7/2001 |
| EP | 0647432 A1 | 4/1995 |

(Continued)

OTHER PUBLICATIONS

Biomet Orthopedics, Inc., Segmental Distal Femur, OSS Orthopedic Salvage System, date not known.
(Continued)

*Primary Examiner* — Suba Ganesan
(74) *Attorney, Agent, or Firm* — Lerner, David, Littenberg, Krumholz & Mentlik, LLP

(57) ABSTRACT

A knee prosthesis includes a femoral component, a tibial component, and a coupling component interconnecting the femoral component and the tibial component. The tibial component includes ball. The femoral component is configured to move relative to the tibial component. The coupling component defines an internal cavity including a first spherical end portion and a second spherical end portion. The internal cavity is dimensioned to receive the ball of the tibial component. The ball is repositioned between the first spherical end portion and the second spherical end portion of the internal cavity upon movement of the femoral component relative to the tibial component.

15 Claims, 26 Drawing Sheets

Related U.S. Application Data division of application No. 12/847,202, filed on Jul. 30, 2010, now Pat. No. 8,545,571.

(52) U.S. Cl.
CPC .......... *A61F 2/3854* (2013.01); *A61F 2/3859* (2013.01); *A61F 2/3886* (2013.01); *A61F 2002/30362* (2013.01); *A61F 2002/30378* (2013.01); *A61F 2220/0033* (2013.01)

(56) References Cited

U.S. PATENT DOCUMENTS

| | | | |
|---|---|---|---|
| 3,688,316 A | 9/1972 | Lagrange et al. | |
| 3,694,821 A | 10/1972 | Moritz | |
| 3,795,922 A | 3/1974 | Herbert et al. | |
| 3,816,853 A | 6/1974 | Elson | |
| 3,824,630 A | 7/1974 | Johnston | |
| 3,837,009 A | 9/1974 | Walker | |
| 3,840,905 A | 10/1974 | Deane | |
| 3,868,730 A | 3/1975 | Kaufer et al. | |
| 3,869,729 A | 3/1975 | Attenborough | |
| 3,885,252 A | 5/1975 | Nakajima | |
| 3,886,600 A | 6/1975 | Kahn et al. | |
| 3,918,101 A | 11/1975 | Lagrange et al. | |
| 3,945,053 A | 3/1976 | Hillberry et al. | |
| 3,969,773 A | 7/1976 | Menschik | |
| 3,996,624 A | 12/1976 | Noiles | |
| 4,001,896 A | 1/1977 | Arkangel | |
| 4,094,017 A | 6/1978 | Matthews et al. | |
| 4,112,522 A | 9/1978 | Dadurian et al. | |
| 4,134,158 A | 1/1979 | Laure | |
| 4,194,250 A | 3/1980 | Walker | |
| 4,213,209 A | 7/1980 | Insall et al. | |
| 4,224,697 A | 9/1980 | Murray et al. | |
| 4,231,122 A | 11/1980 | Koeneman | |
| 4,268,920 A | 5/1981 | Engelbrecht et al. | |
| 4,298,992 A | 11/1981 | Burstein et al. | |
| 4,358,859 A | 11/1982 | Schurman et al. | |
| 4,662,889 A | 5/1987 | Lichner et al. | |
| 4,834,758 A | 5/1989 | Lane et al. | |
| 4,865,606 A | 9/1989 | Rehder | |
| 5,098,436 A | 3/1992 | Ferrante et al. | |
| 5,116,376 A | 5/1992 | May | |
| 5,123,928 A | 6/1992 | Moser | |
| 5,312,411 A | 5/1994 | Steele et al. | |
| 5,413,607 A | 5/1995 | Engelbrecht et al. | |
| 5,458,644 A | 10/1995 | Grundei | |
| 5,549,687 A | 8/1996 | Coates et al. | |
| 5,755,804 A | 5/1998 | Schmotzer et al. | |
| 5,810,829 A | 9/1998 | Elliott et al. | |
| 5,824,102 A | 10/1998 | Buscayret | |
| 5,954,770 A | 9/1999 | Schmotzer et al. | |
| 6,117,175 A | 9/2000 | Bosredon | |
| 6,123,723 A | 9/2000 | Konya et al. | |
| 6,132,467 A | 10/2000 | Keller | |
| 6,165,223 A | 12/2000 | Metzger et al. | |
| 6,210,444 B1 | 4/2001 | Webster et al. | |
| 6,264,696 B1 | 7/2001 | Reigner et al. | |
| 6,319,283 B1 | 11/2001 | Insall et al. | |
| 6,475,241 B2 | 11/2002 | Pappas | |
| 6,485,519 B2 | 11/2002 | Meyers et al. | |
| 6,488,711 B1 | 12/2002 | Grafinger | |
| 6,582,469 B1 | 6/2003 | Tornier | |
| 6,629,999 B1 | 10/2003 | Serafin, Jr. | |
| 6,699,291 B1 | 3/2004 | Augoyard et al. | |
| 6,719,800 B2 | 4/2004 | Meyers et al. | |
| 6,740,092 B2 | 5/2004 | Lombardo et al. | |
| 6,764,516 B2 | 7/2004 | Pappas | |
| 6,773,461 B2 | 8/2004 | Meyers et al. | |
| 6,797,005 B2 | 9/2004 | Pappas | |
| 6,984,249 B2 | 1/2006 | Keller | |
| 6,986,791 B1 | 1/2006 | Metzger | |
| 7,081,137 B1 | 7/2006 | Servidio | |
| 7,153,327 B1 | 12/2006 | Metzger | |
| 7,160,330 B2 | 1/2007 | Axelson, Jr. et al. | |
| 7,232,465 B2 | 6/2007 | Keller | |
| 7,326,252 B2 | 2/2008 | Otto et al. | |
| 7,837,737 B2 | 11/2010 | Hedley et al. | |
| 7,963,968 B2 | 6/2011 | Dees, Jr. | |
| 8,187,280 B2 | 5/2012 | May et al. | |
| 2002/0103541 A1 | 8/2002 | Meyers et al. | |
| 2002/0107576 A1 | 8/2002 | Meyers et al. | |
| 2003/0009228 A1 | 1/2003 | Meyers et al. | |
| 2003/0009229 A1 | 1/2003 | Pappas | |
| 2003/0216809 A1 | 11/2003 | Ferguson | |
| 2004/0186583 A1 | 9/2004 | Keller | |
| 2004/0186584 A1 | 9/2004 | Keller | |
| 2004/0220676 A1 | 11/2004 | Keller | |
| 2004/0249467 A1 | 12/2004 | Meyers et al. | |
| 2005/0107886 A1 | 5/2005 | Crabtree et al. | |
| 2005/0192672 A1 | 9/2005 | Wyss et al. | |
| 2005/0246028 A1 | 11/2005 | Pappas et al. | |
| 2005/0278035 A1* | 12/2005 | Wyss .................... | A61F 2/3868 623/20.27 |
| 2007/0135925 A1* | 6/2007 | Walker .................. | A61F 2/3859 623/20.21 |
| 2008/0004708 A1 | 1/2008 | Wyss | |
| 2008/0097616 A1 | 4/2008 | Meyers et al. | |
| 2008/0167722 A1 | 7/2008 | Metzger et al. | |
| 2009/0319048 A1* | 12/2009 | Shah ........................ | A61F 2/38 623/20.29 |
| 2011/0040387 A1* | 2/2011 | Ries ...................... | A61F 2/3868 623/20.27 |
| 2012/0029649 A1 | 2/2012 | Collazo et al. | |
| 2012/0078260 A1 | 3/2012 | Fearon et al. | |

FOREIGN PATENT DOCUMENTS

| | | |
|---|---|---|
| FR | 2701387 A1 | 8/1994 |
| FR | 2758456 A1 | 7/1998 |
| GB | 2035090 A | 6/1980 |
| GB | 2088724 A | 6/1982 |
| GB | 2129306 A | 5/1984 |
| GB | 2296443 A | 7/1996 |

OTHER PUBLICATIONS

Howmedica, Inc. The Sphero-Centric Knee, 1975.
International Search Report Application No. PCT/US2011/045663, dated Oct. 24, 2011.
Johnson&Johnson, S-Rom NOILES, website printout, Mar. 3, 2009.
Link Orthopaedics, Lombardi, Joint Implant Surgeons, Inc., Surgical Technique with the Link Endo-Model rotational Knee System (Non-Modular), Pine Brook, NJ 2000.
Smith & Nephew, RT-PLUS Solution Modular, date not known.
Stryker, GMRS Global Modular Replacement System, date not known.
Wright, Guardian Revision Hinge Knee System, date not known.
Zimmer, NexGen Rotating Hinge Knee, 2002.

\* cited by examiner

STABILIZED KNEE PROSTHESIS

CROSS-REFERENCE TO RELATED APPLICATIONS

This application is a continuation of U.S. patent application Ser. No. 14/027,636, filed on Sep. 16, 2013, which is a divisional of U.S. application Ser. No. 12/847,202, filed on Jul. 30, 2010, the disclosures of which are incorporated herein by reference.

BACKGROUND OF THE INVENTION

The present disclosure relates to orthopedics devices and, more particularly, to knee prostheses.

During articulation of a natural knee joint, flexion between the tibia and the femur takes place about a transverse axis while some relative rotation between the tibia and the femur occurs about a longitudinal axis. Such flexion and rotation is necessary to carry out a normal gate cycle. It has been established that in full extension the tibia is rotationally displaced, relative to the femur, by approximately 2-3 degrees. As the natural knee flexes, the tibia rotates internally. According to previous studies, about 5 degree of rotation ordinarily occurs as the knee is articulated from 0 degree to 10 degree of flexion; thereafter, little further rotation occurs up to at least about 45 degree of flexion. Total rotation at 110 degrees of flexion is approximately 20 degrees.

Rotational stability of the natural knee is provided by the collateral and cruciate ligaments. The cruciate ligaments deter uncontrolled internal rotation within a certain range of flexion of the knee, while the collateral ligaments provide transverse stability and deter uncontrolled external rotation of the tibia. Where the natural knee is replaced by a total knee prosthesis, either the anterior cruciate ligament or both the anterior and posterior cruciate ligaments ordinarily are sacrificed. In the instances where the knee prosthesis is constrained to supply the stability ordinarily provided by the sacrificed ligaments, it is desirable for the knee prosthesis to mimic the natural knee as closely as possible.

Although several knee prostheses have been developed over the years, improvements are still possible. A need exists for knee prostheses capable of more closely imitating the natural knee.

As used herein, when referring to bones or other parts of the body, the term "proximal" means closer to the heart and the term "distal" means more distant from the heart. The term "inferior" means towards the feet and the term "superior" means towards the head. The term "anterior" means towards the front part of the body or the face and the term "posterior" means towards the back of the body. The term "medial" means towards the midline of the body and the term "lateral" means away from the midline of the body.

BRIEF SUMMARY OF THE INVENTION

The present disclosure relates to a knee prosthesis for implantation in a knee joint. In one embodiment, the knee prosthesis includes a femoral component, a tibial component, and a coupling component mounted on the femoral component and interconnecting the femoral component and the tibial component. The tibial component includes a ball. The femoral component is configured to move relative to the tibial component. The coupling component defines an internal cavity including a first spherical end portion and a second spherical end portion. The internal cavity is dimensioned to receive the ball of the tibial component. The ball is repositioned between the first spherical end portion and the second spherical end portion of the internal cavity upon movement of the femoral component relative to the tibial component.

In an alternate embodiment, the knee prosthesis includes a femoral component, a tibial component including a ball and a coupling component. The femoral component is configured to articulate relative to the ball of the tibial component. The coupling component connects the femoral component to the tibial component and defines an internal cavity including a first cavity portion and a second cavity portion. Each of the first and second cavity portions is dimensioned to receive the ball. The first and second cavity portions are in communication with each other. The coupling component moves upon articulation of the femoral component relative to the tibial component between a first position where the ball is positioned in the first cavity portion and a second position where the ball is positioned in the second cavity portion.

In an alternate embodiment, the knee prosthesis includes a femoral component, a tibial component, and a coupling component movably interconnecting the femoral component to the tibial component. The femoral component includes a housing with an anterior wall. The coupling component includes a first post and a second post at least partially positioned within the first post. The first post has a protrusion configured to engage the anterior wall of the housing during hyperextension of a knee. The coupling component may be monolithically formed with at least a portion of the tibial component.

BRIEF DESCRIPTION OF THE DRAWINGS

The present disclosure may be better understood with reference to the following drawings and description. The components in the figures are not necessarily to scale, emphasis instead being placed upon illustrating the principles of the presently disclosed knee prosthesis. Moreover, in the figures, like reference numerals designate corresponding parts throughout the different views.

DETAILED DESCRIPTION

Figure 1:
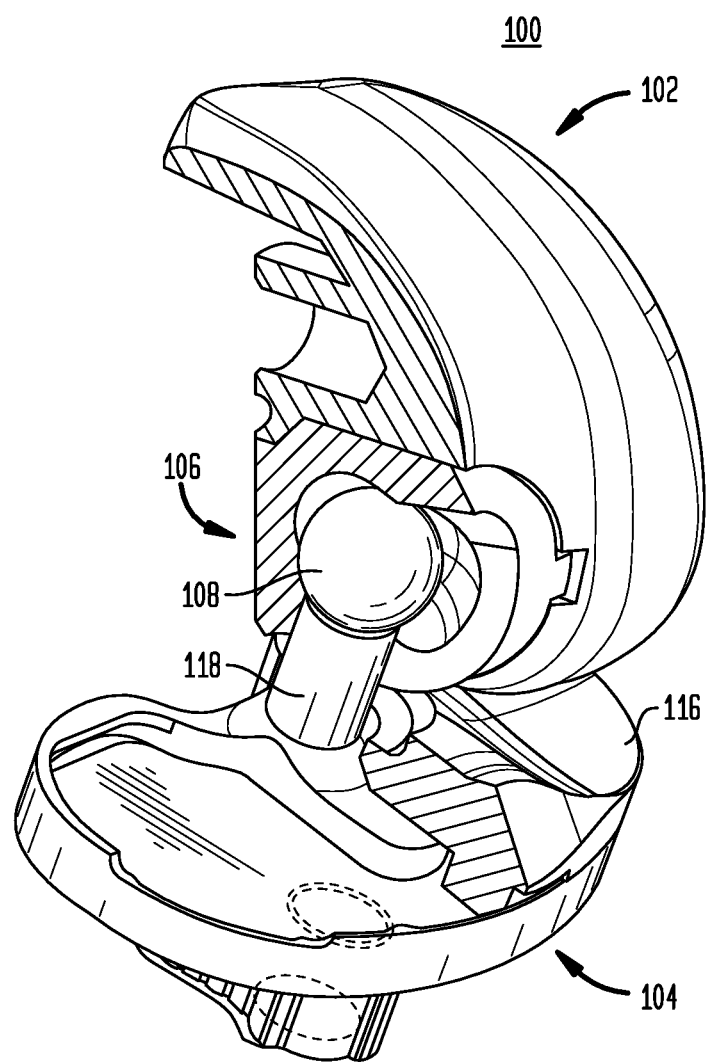
FIG. 1. is an isometric cut-away view of a knee prosthesis according to an embodiment of the present disclosure.
Figure 2:
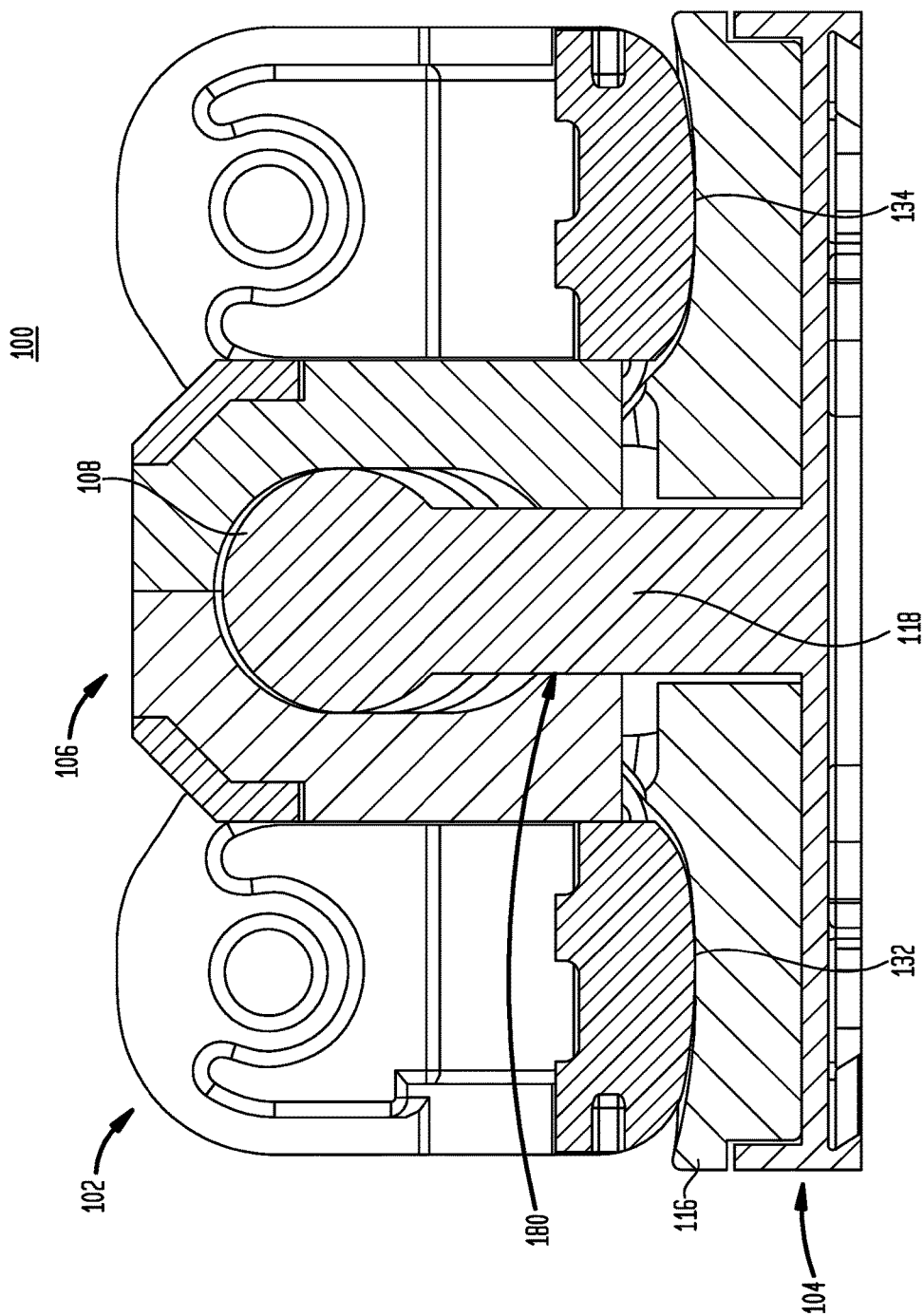
FIG. 2 is a cross-sectional view, taken along a plane parallel to the coronal plane, of the knee prosthesis of FIG. 1.

FIGS. 1 and 2 depict an embodiment of a stabilized knee prosthesis 100 for replacing a natural knee joint. In some embodiments, knee prosthesis 100 includes a femoral component 102, a tibial component 104, and a coupling component 106 interconnecting the femoral component 102 and tibial component 104. In operation, femoral component 102 can articulate relative to tibial component 104 or bearing component 116 and coupling component 106 rotates with femoral component 102, as discussed in detail below. Coupling component 106 controls the rotation of the femoral component 102 as it articulates in relation to tibial component 104. Femoral component 102 has condyles that articulate on the condylar tracks of the bearing component 116 of the tibial component 104. Tibial component 104 is adapted to be attached to a proximal end of a tibia, whereas femoral component 102 is adapted to be attached to a distal end of a femur in a well known manner Both the distal end of the femur and the proximal end of the tibia may be resected or prepared before implantation of knee prosthesis 100. In some embodiments, knee prosthesis 100 is wholly or partly made of a substantially rigid material, such as titanium, titanium alloy, chrome-cobalt alloy, cobalt-chromium-molybdenum alloys (e.g., cobalt-chromium-molybdenum alloy sold under the trademark Vitallium®), polyethylene, polyether ether ketone (PEEK), or any suitable metal or polymer. Bearing component 116 is primarily made of ultra high molecular weight polyethylene (UHMWPE).

Tibial component 104 includes a ball or spherical member 108 for facilitating articulation of femoral component 102 relative to tibial component 104. Ball 108 may have a spherical shape or any other suitable shape (e.g., oblong shape). Coupling element 106 substantially encloses or surrounds ball 108 of tibial component 104. Femoral component 102 surrounds at least a portion of coupling component 106. In some embodiments, femoral component 102 substantially encloses coupling component 106. In any case, femoral component 102 is fixed relative to coupling component 106 and, consequently, femoral component 102 and coupling component 106 move concomitantly.

Figure 3:
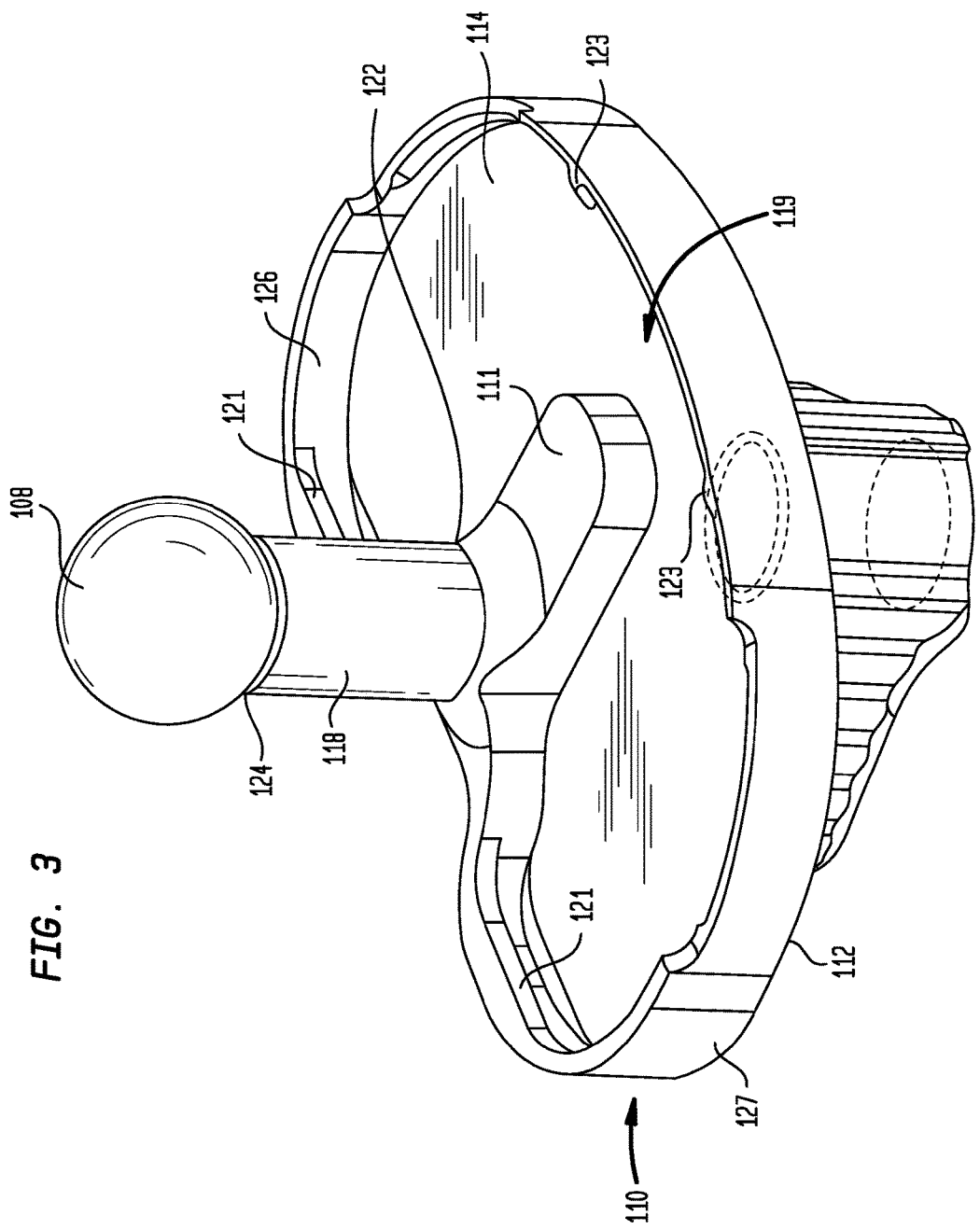
FIG. 3 is an isometric view of a tibial baseplate of the knee prosthesis of FIG. 1.

With reference to FIG. 3, tibial component 104 includes a baseplate 110 incorporating an intercondylar support 111 to support, among other things, a post 118 attached to ball 108. Baseplate 110 may have a substantially oblong shape matching the proximal tibia and includes a distally facing bone contacting bottom portion 112 for engaging the proximal tibia and a proximally facing top portion 114 for engaging and supporting a tibial bearing insert or component 116 (see FIG. 4). The top portion 114 of baseplate 110 includes sides 126, 127 defining an opening 119 for supporting tibial bearing insert 116. Sides 126, 127 of baseplate 110 are oriented in directly opposite relationship with respect to each other and are oriented medially or laterally depending on whether the baseplate 110 is on the left or right tibia. In addition, sides 126, 127 of baseplate 110 include extensions 121 and 123 for locking tibial bearing insert 116 on baseplate 110. Central support 111 extends into opening 119 defined by baseplate 110. Support 111 assists in locating tibial bearing insert 116 when tibial bearing insert 116 is assembled with baseplate 110. Opening 119 is dimensioned for receiving the bottom surface 128 of tibial bearing insert 116, shown in FIG. 4. Connecting post 118 extends from support 111 and couples ball 108 to baseplate 110. In particular, connecting post 118 has a first end 122 connected to support 111 and a second end 124 connected to ball 108. In some embodiments, connecting post 118 has a substantially cylindrical shape. Irrespective of its shape, connecting post 118 is made wholly or partly of a substantially rigid material. Post 118 may be modular and/or ball 108 may have different sizes to provide variation in the proximal-distal location of ball 108.

Figure 4:
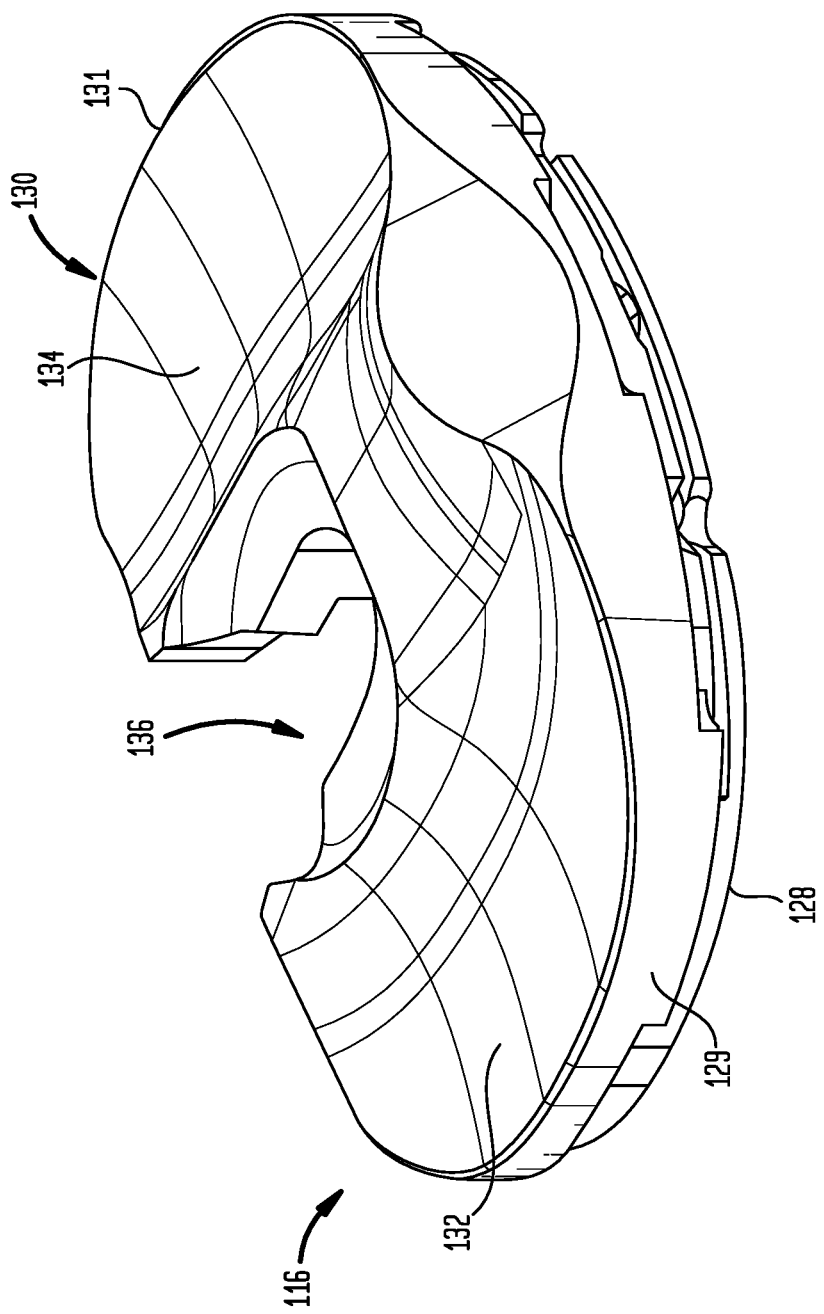
FIG. 4 is an isometric view of a tibial insert of the knee prosthesis of FIG. 1.

As shown in FIG. 4, tibial component 104 further includes a tibial bearing insert 116 for facilitating articulation of femoral component 102 relative to tibial component 104. Tibial bearing insert 116 includes a side portions 129, 131 and a distally facing bottom portion 128 for securely engaging the top portion 114 of baseplate 110 and a proximally facing top portion 130 for providing a bearing surface for supporting at least a condylar portion of femoral component 102. First and second portions 128, 130 are oriented in a directly opposite relationship to each other. Top portion 130 has a first depression or undulation or medial condyle track 132 and a second depression or undulation or lateral condyle track 134. Each of first and second undulations 132, 134 is adapted to receive and support a condyle of femoral component 102. Between first and second respective condylar depressions 132, 134, tibial insert 116 defines a clearance slot 136 dimensioned for securely receiving connecting post 118 of baseplate 110.

Figure 5:
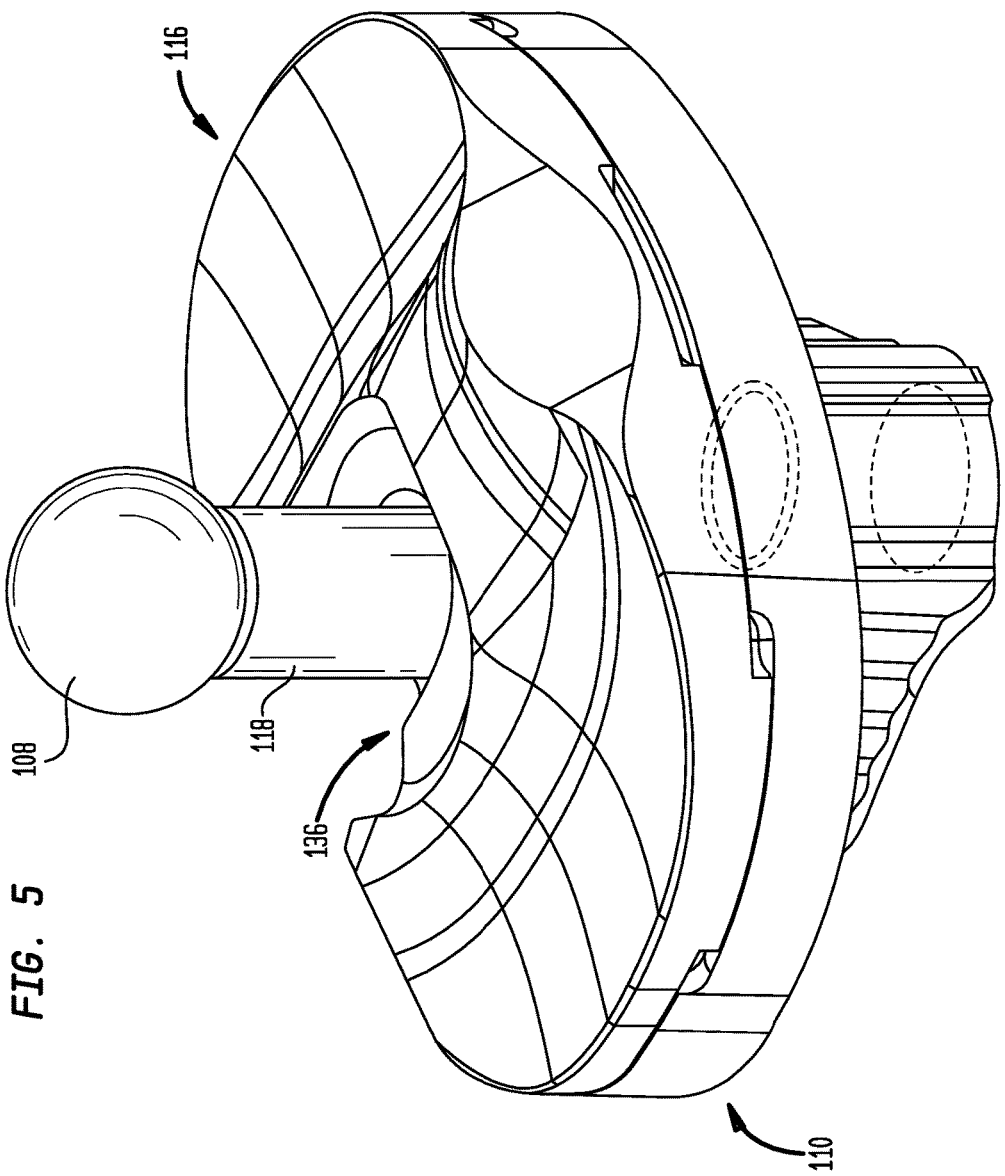
FIG. 5 is an isometric view of a tibial component including the tibial baseplate and the tibial insert assembled together.

Clearance slot 136 facilitates assembly of tibial bearing insert 116 onto baseplate 110. During assembly, distal side 128 of tibial bearing insert 116 is placed and locked to proximal surface 114 of baseplate 110 via extensions 121, 123. Connecting post 118 is allowed to pass through clearance slot 136. After assembly, a distal portion of connecting post 118 is received within clearance slot 136, as seen in FIG. 5. FIG. 5 also shows that, in an assembled tibial component 104, ball 108 is spaced proximally from tibial bearing insert 116.

Figure 6:
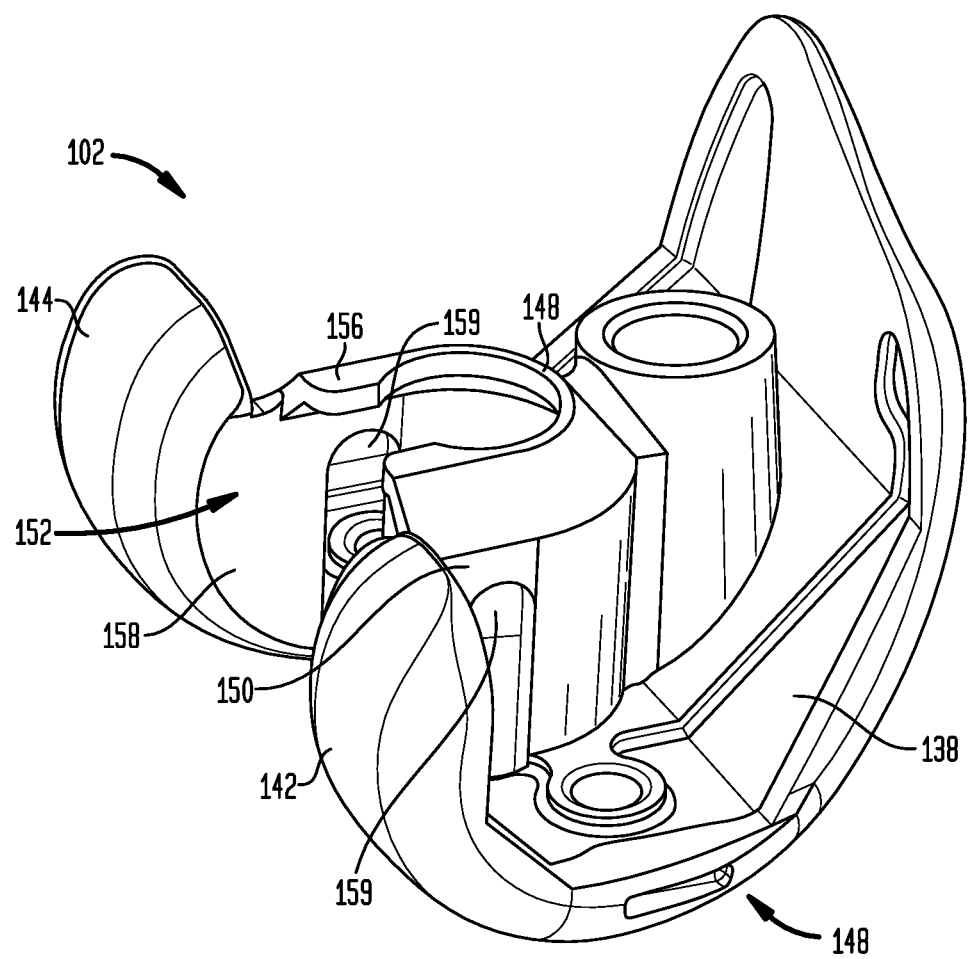
FIG. 6 is an isometric proximal view of a femoral component of the knee prosthesis of FIG. 1.
Figure 7:
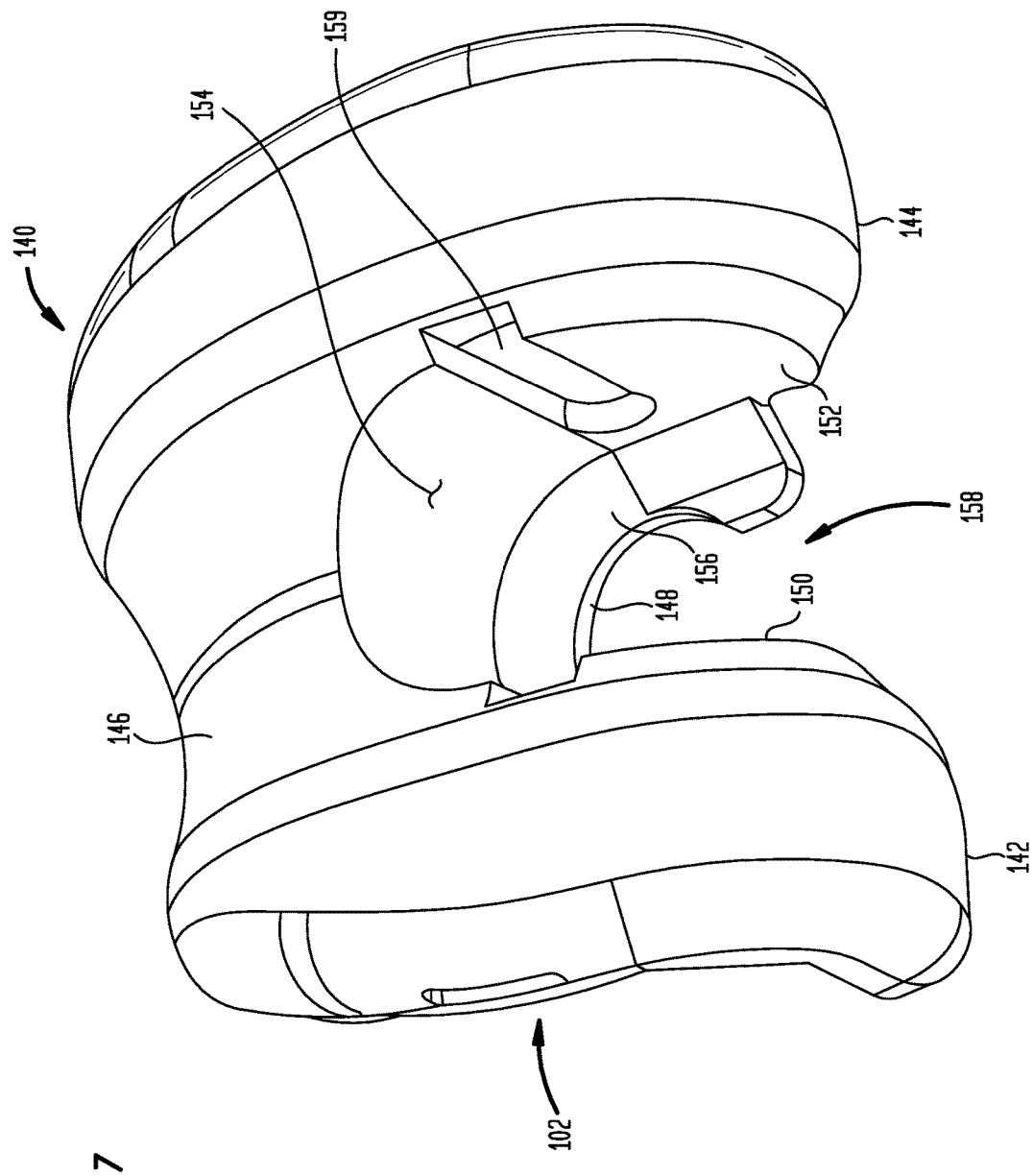
FIG. 7 is an isometric distal view of the femoral component of FIG. 6.

Referring to FIGS. 6 and 7, femoral component 102 includes a proximal first side 138 for securely engaging the distal end of a distal femur and a second side 140 oriented in a directly opposite relationship to first side 138 and forming the condylar bearing surface of femoral component 102. Second side 140 of femoral component 102 includes a first or medial condyle 142 and a second or lateral condyle 144. As seen in FIG. 7, first and second condyles 142, 144 have the typical arcuate configuration and are oriented substantially parallel to each other. As discussed above, first and second condyle tracks 132, 134 are configured to receive first and second condyles 142, 144, respectively. Second side 140 of femoral component 102 further includes a anteriorly facing patella track 146 located between first and second condyles 142, 144 and adapted to receive a patellar implant (not shown).

First or proximally facing side 138 of femoral component 102 further includes a proximally extending housing 148 located on a proximal facing surface of a distal region of femoral component 102 and between first and second condyles 142, 144. Housing 148 includes a medial wall 150 adjacent to medial condyle 142, a lateral wall 152 adjacent to lateral condyle 144, an anterior wall 154 and a proximal wall 156. Anterior and proximal walls 154, 156 both connect the medial and lateral walls 150, 152. Housing 148 defines an opening 158 dimensioned for receiving coupling component 106 and at least a portion of connecting post 118. Opening 158 is located in the posterior region of the femoral component 102 between medial and lateral condyles 142, 144. Walls 150, 152 of femoral component 102 include guide slots apertures 159, which function will be discussed below.

Figure 8:
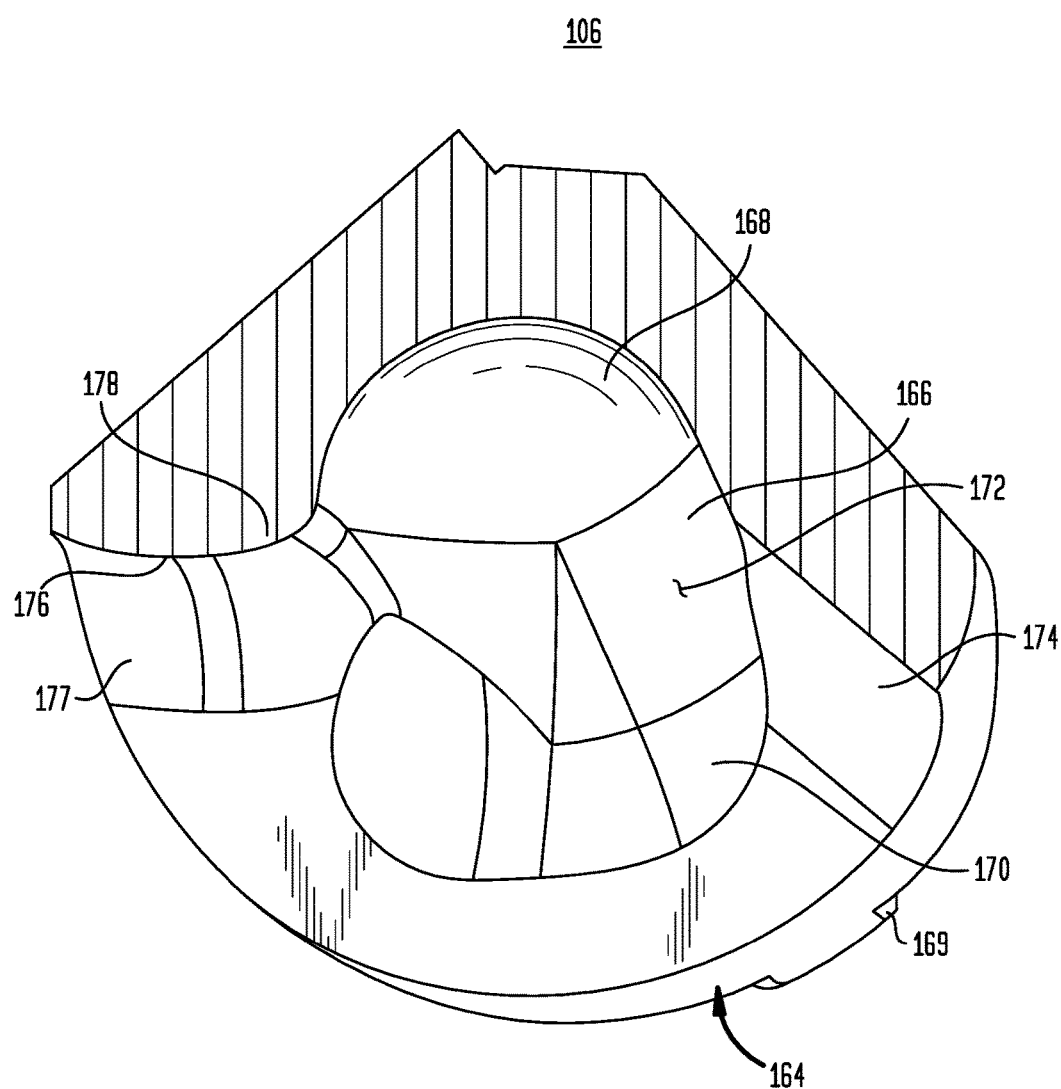
FIG. 8 is a side cross-sectional view of a coupling component of the knee prosthesis of FIG. 1.
Figure 9:
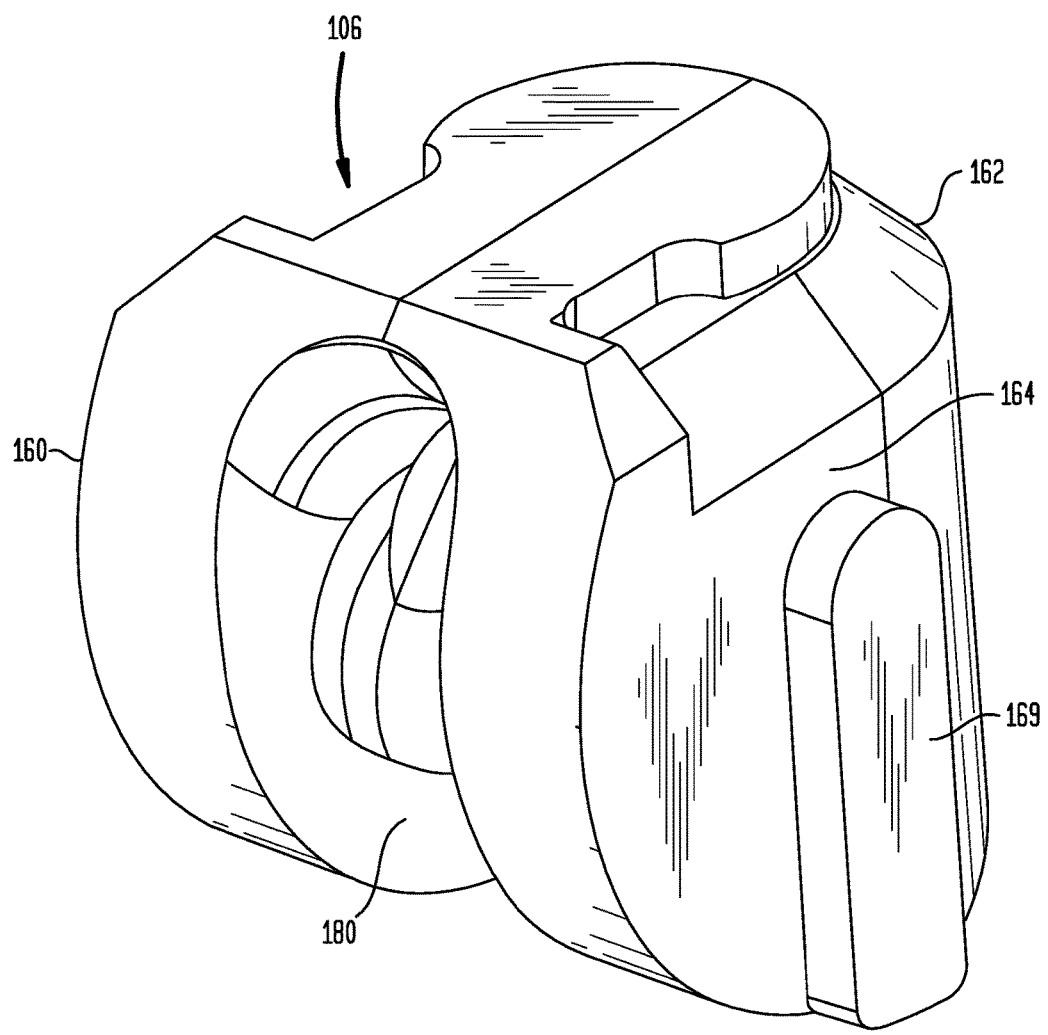
FIG. 9 is an isometric view of the coupling component of FIG. 8.

With reference to FIGS. 8 and 9, there is shown a coupling component 106 which is mounted on femoral component 102 and receives ball 108, which connects femoral component 102 to tibial component 104. In some embodiments, coupling component 106 may have two parts such as first section 160 and a second section 162, but coupling component 106 may be formed of a one-piece monolithic structure. First and second sections 160, 162 may be symmetrical halves or asymmetrical parts. In any case, first and second sections 160, 162 collectively form coupling component 106. In the embodiment depicted in FIG. 9, coupling component 106 defines a centrally located slot 180 between first and second sections 160, 162. As seen in FIG. 2, slot 180 is dimensioned to closely fit connecting post 118. In addition to slot 180, coupling component 106 has an outer surface 164 adapted for securely engaging housing 148 of femoral component 102 and forms an internal pocket or cavity 166 dimensioned for receiving ball 108 of tibial component 104. Coupling component 106 further includes a pair of extensions 169 which are received within apertures 159 of housing 148. Extensions 169 extend outwardly from outer surface 164.

As best seen in the cross-section of FIG. 8, internal cavity 166 includes a first cavity portion or spherical end portion 168, a second cavity portion or spherical end portion 170, and a longitudinal portion 172 coupling the first and second spherical end portions 168, 170. In certain embodiments, longitudinal portion 172 has a substantially cylindrical shape. First and second cavity portions 168, 170 may have a spherical shape as well as any other suitable shapes. The spherical shape of cavity end portions 168, 170 may match ball 108. Longitudinal portion 172, first spherical end portion 168 and second spherical end portion 170 may have substantially similar or identical diameters to allow a smooth reposition of ball 108 within internal cavity 166 during articulation of femoral component 102 in relation to tibial component 104. Internal cavity 166 also includes an elongated portion 177 dimensioned for receiving at least a portion of connecting post 118.

Coupling component 106 defines a slot 180 adjacent to internal cavity 166. Slot 180 terminates at two ends (i.e., a first end 174 and a second end 176.) First end 174 may have a radius of about one-half the width of slot 180. Second end 176 includes a series of curved surfaces defining a cam 178. Cam 178 is configured to engage connecting post 118 upon articulation of femoral component 102 relative to tibial component 104. When cam 178 engages connecting post 118, ball 108 is repositioned from first spherical end portion 168 to second spherical end portion 170 due to the movement of femoral component 102 with respect to tibial component 104 from extension to flexion, as discussed in detail below.

Figure 10:
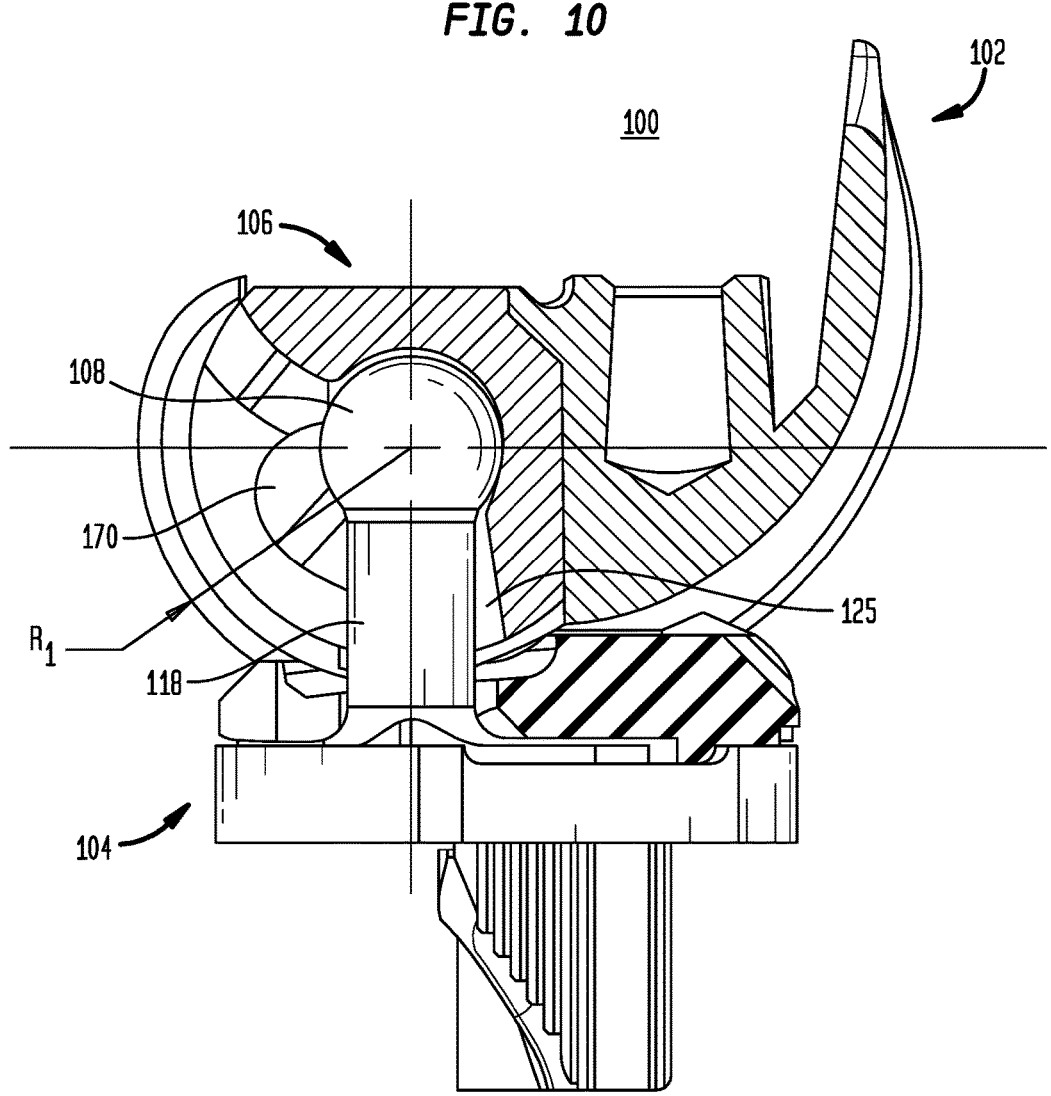
FIG. 10 is a side cross-sectional view of the knee prosthesis of FIG. 1 in full extension.
Figure 11:
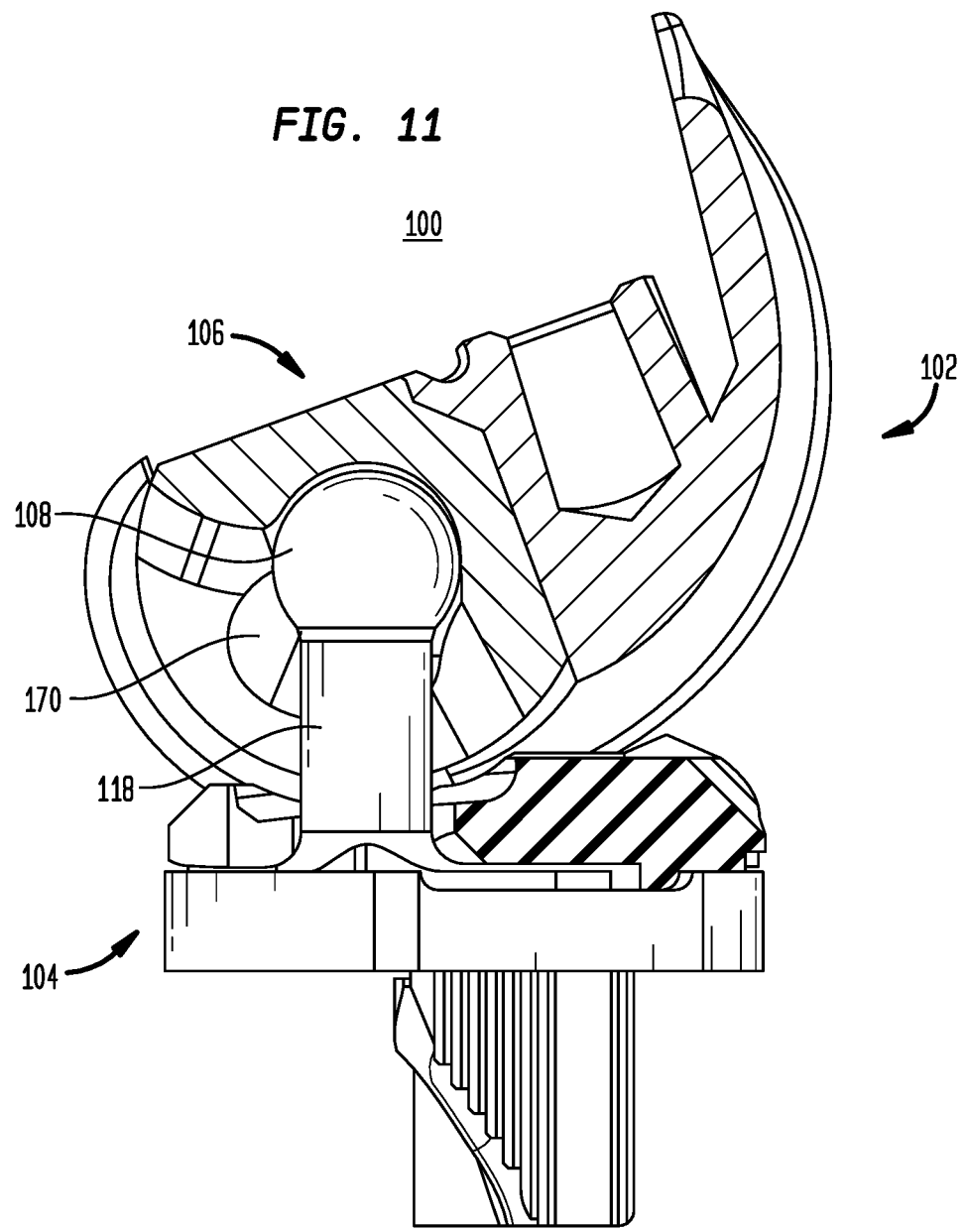
FIG. 11 is a side cross-sectional view of the knee prosthesis of FIG. 1 in a 20 degree extension.
Figure 12:
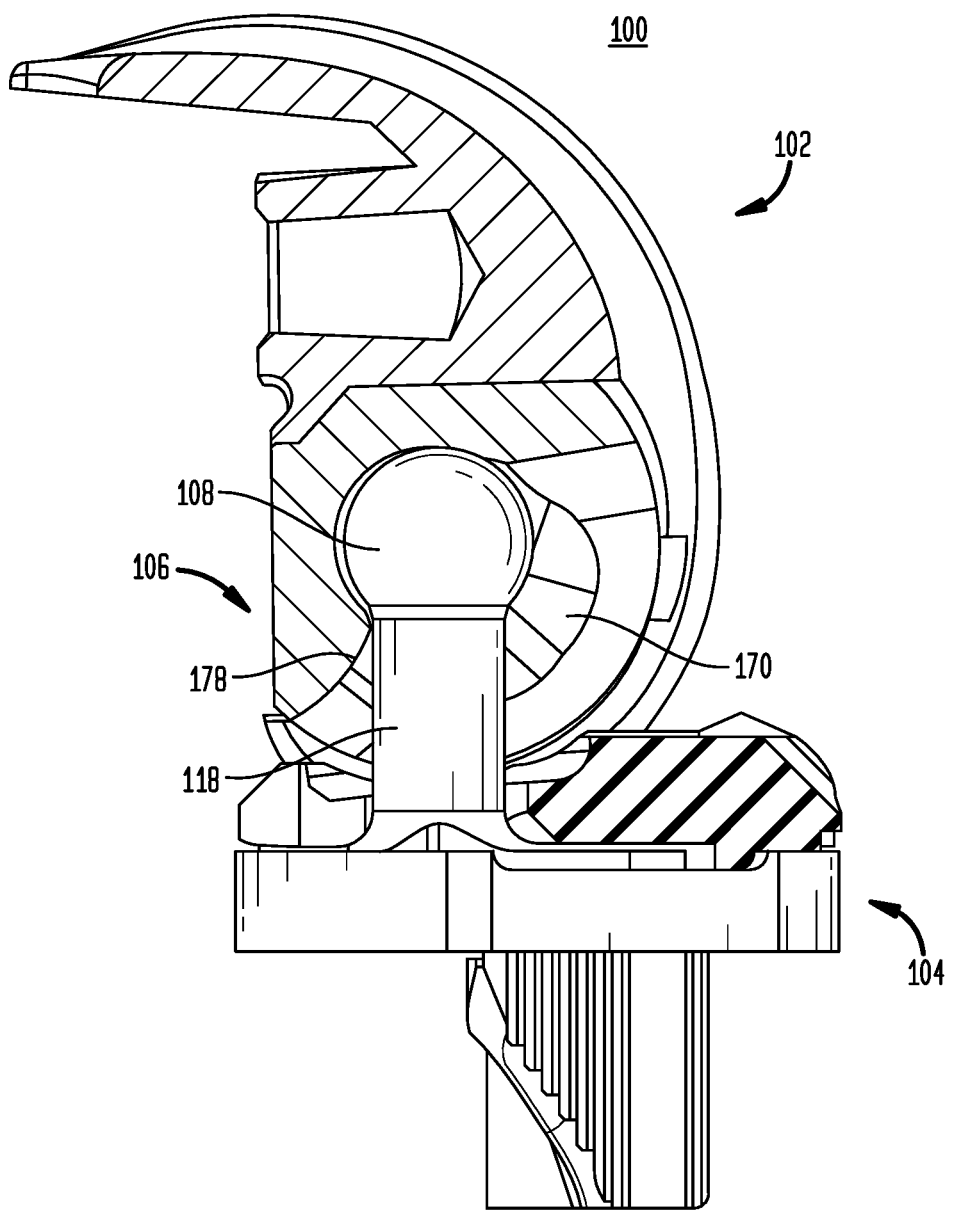
FIG. 12 is a side cross-sectional view of the knee prosthesis of FIG. 1 in a 90 degree extension.
Figure 13:
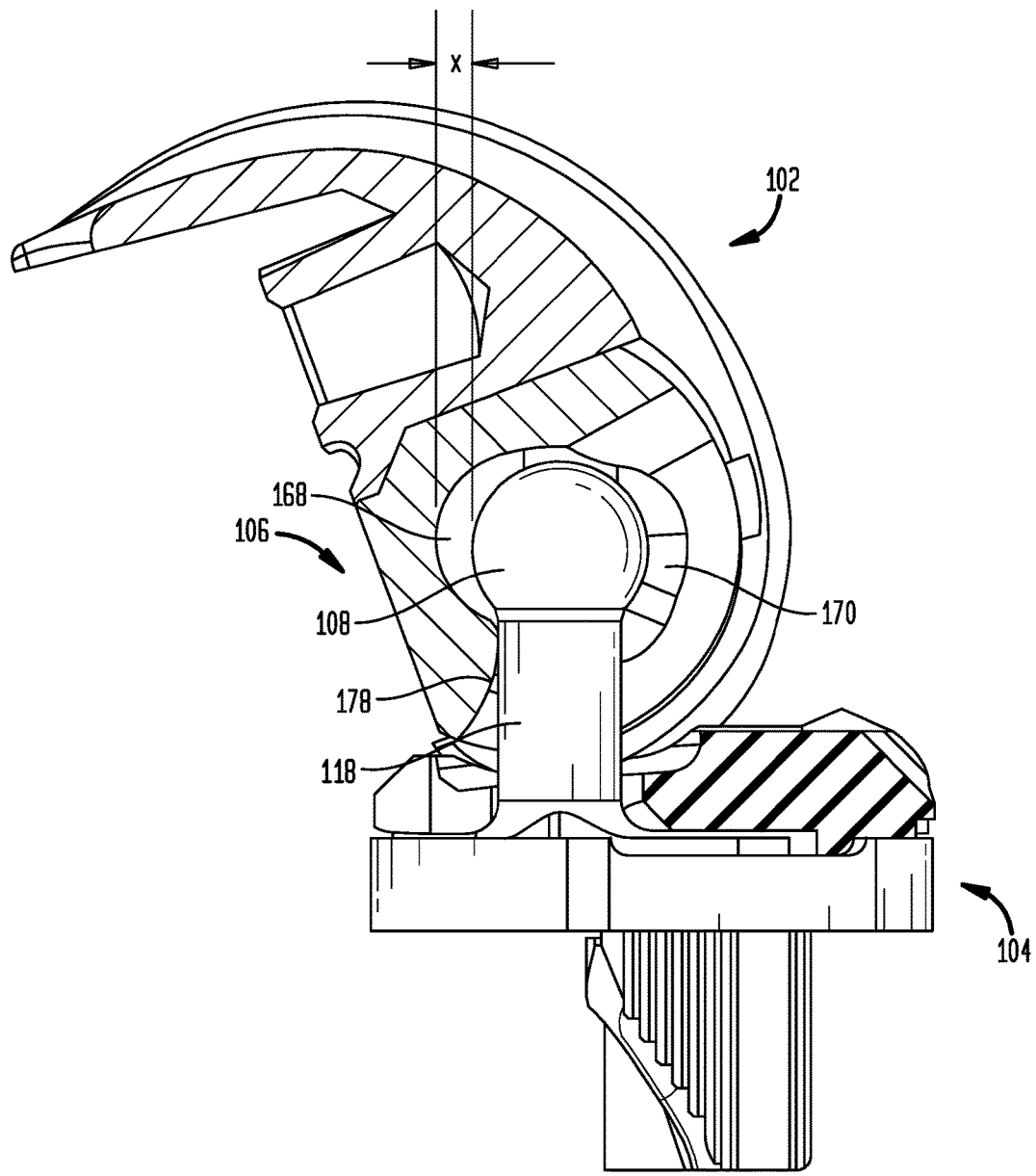
FIG. 13 is a side cross-sectional view of the knee prosthesis of FIG. 1 in a 110 degree extension.
Figure 14:
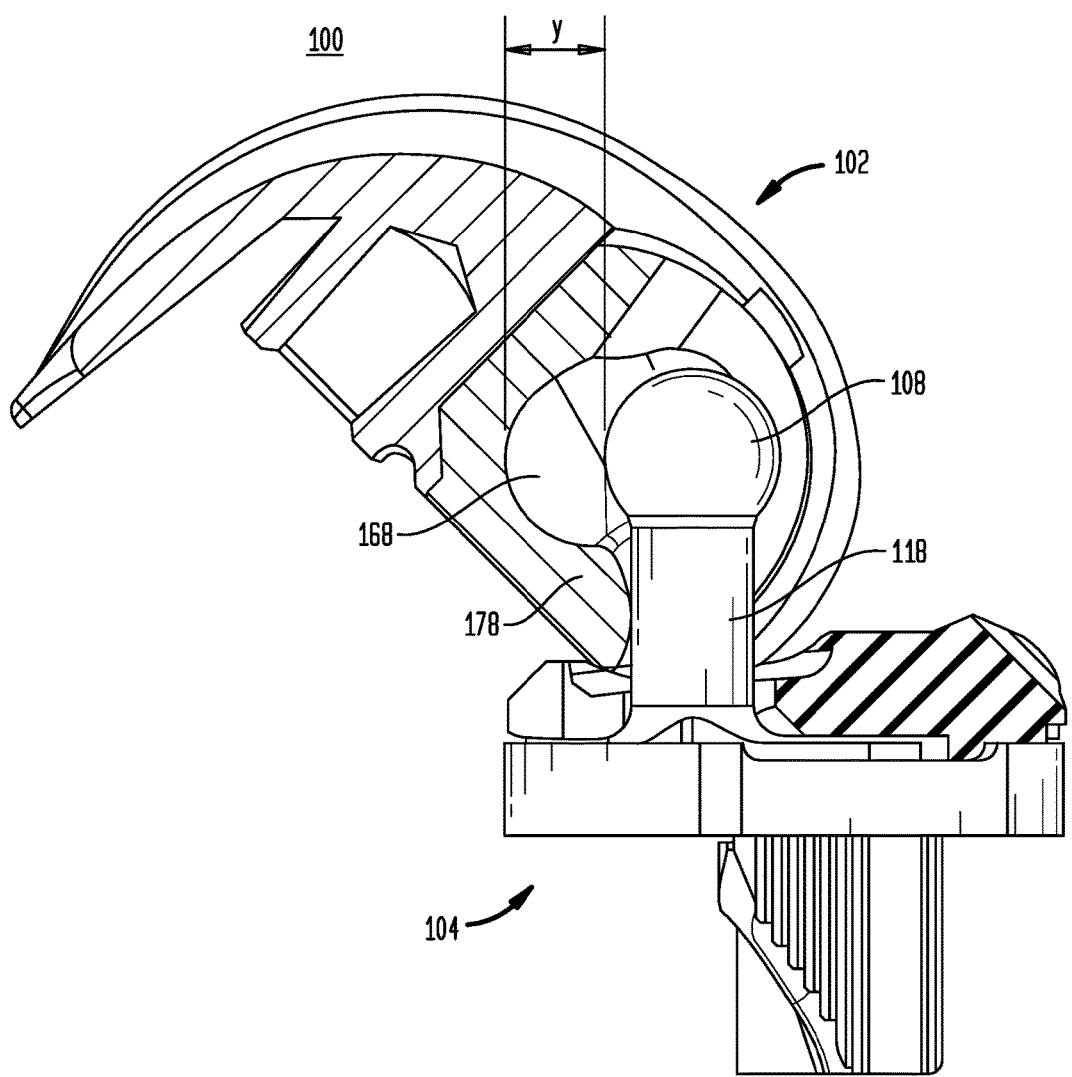
FIG. 14 is a side cross-sectional view of the knee prosthesis of FIG. 1 in a 135 degree extension.

As seen in FIGS. 10-14, knee prosthesis 100 substantially mimics the kinematics of the natural knee because of the location of ball 108 with respect to the flexion axis and the rotary arc. U.S. Pat. No. 7,160,330, the entire contents of which are incorporated herein by reference, describes in detail the flexion axis and the rotary arc. When knee prosthesis 100 is implanted in a patient, femoral component 102 articulates with respect to tibial component 104 during flexion. During flexion of knee prosthesis 100, coupling component 106 moves along with femoral component 102 and, consequently, ball 108 is repositioned between a first position in full extension and a second position in full flexion. In the first extended position, ball 108 is located in spherical end portion 168, as seen in FIG. 10. In the second flexed position, ball 108 is located in spherical end portion 170, as shown in FIG. 14. While knee prosthesis 100 flexes from extension to full flexion, ball 108 is situated in a plurality of positions between the first and second spherical end portions 168 and 170. Thus, ball 108 may be located at least partially at various positions along longitudinal portion 172 of internal cavity 166 between first and second spherical end portions 168, 170, as depicted in FIG. 13.

Figure 15:
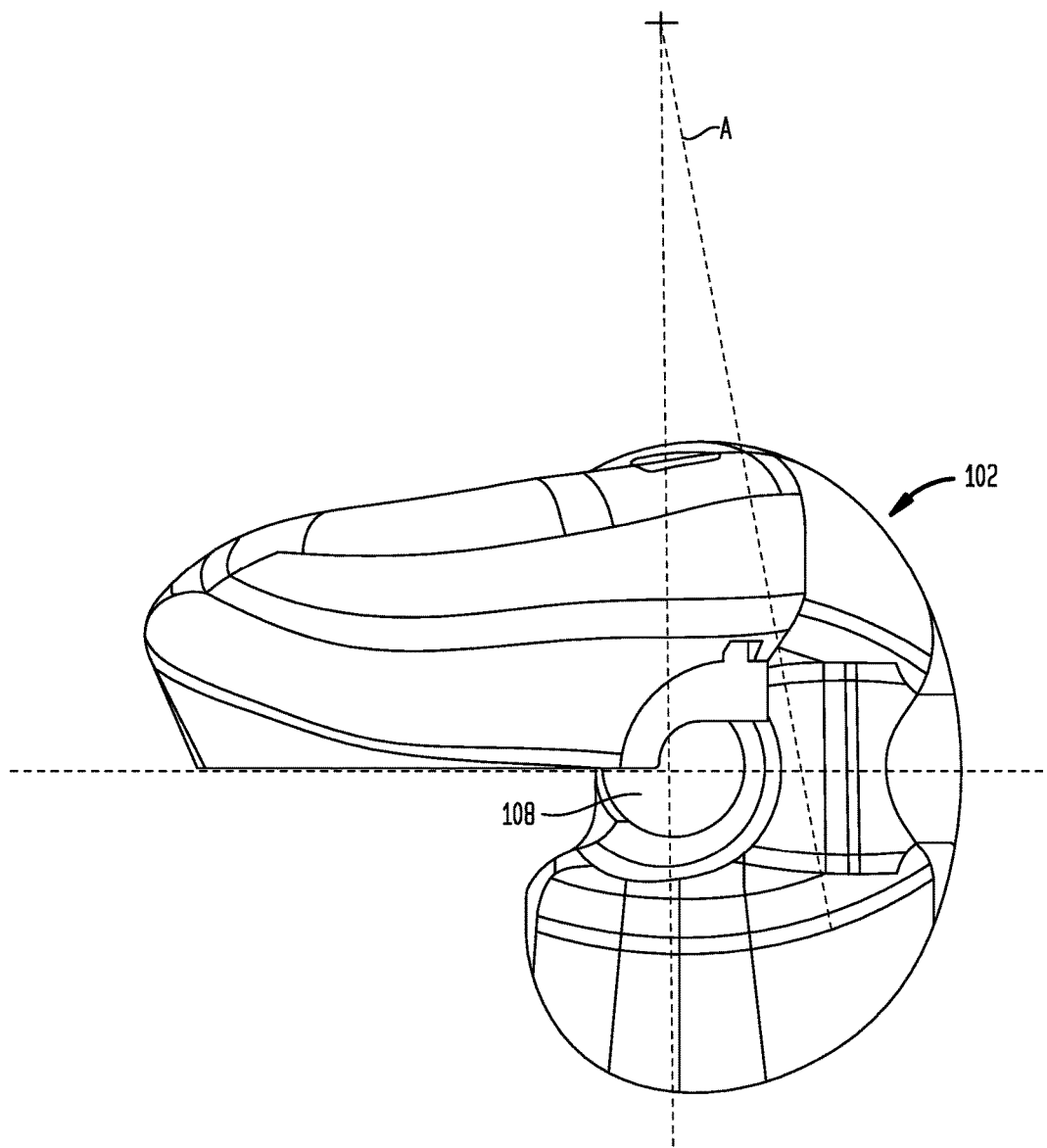
FIG. 15 is a superior view of the knee prosthesis of FIG. 1.

FIG. 10 shows femoral component 102 in full extension with respect to tibial component (i.e., 0 degree flexion). In the full extension position, ball 108 of tibial component 104 is located in first spherical end 168 of internal cavity 166. As seen in FIG. 10, when knee prosthesis 100 has an open space 125 between connecting post 118 and coupling component 106 that allows hyperextension (e.g., 15 degrees) of the knee. When femoral component 102 rotates 20 degree (i.e., 20 degree flexion) relative to tibial component 104, as seen in FIG. 11, ball 108 remains in the first spherical end portion 168 of internal cavity 166. As femoral component 102 moves between 20 and 135 degrees of flexion, the flexion axis of the medial and lateral condyles 142, 144 coincides with the centerline of ball 108. The alignment between the flexion axis of the medial and lateral condyles 142, 144 and the centerline of ball 108 facilitates smooth rotation and allows compressive loads to be transferred to the articular surface of the tibia throughout the range of motion. Despite facilitating movement, this alignment prevents, or at least inhibits, anterior-posterior ("A-P") displacement, because ball 108 is captured in first spherical end portion 168 of internal cavity 166. In any event, the position of ball 108 allows flexion, reasonably restoring the function of the cruciate ligaments. As seen in FIG. 15, the centerline of ball 108 is aligned with the center plane of rotary arc A defined the trajectory of femoral component 102 with respect to tibial component 104. Such alignment allows the femur to internally and externally rotate as required during flexion and extension.

Knee prosthesis 100 may be assembled prior or during an operation. All components of knee prosthesis 100 are sized so that they can be snapped together. Accordingly, operators may assemble knee prosthesis 100 without any tools. In one exemplary method of assembly, an operator snaps the first side 128 of tibial bearing insert 116 onto the proximal surface 114 of baseplate 110 via extensions 121, 123, thereby locking tibial bearing insert 116 to baseplate 110 as seen in FIG. 5. While tibial bearing insert 116 is being locked to baseplate 110, the connecting post 118 of baseplate 110 is allowed to pass through the clearance slot 136 of tibial bearing insert 116. Coupling component 106 can also be mounted within the housing 148 of femoral component 102. To this end, the operator may slide extensions 169 of coupling component 106 through elongated apertures 159 of housing 148 until coupling component 106 is securely attached to femoral component 102. Ball 108 of baseplate 110 is then snapped into the internal cavity 166 of coupling component 106. As discussed in detail below, knee prosthesis 100 may use different kinds of coupling components. These coupling components 106 can be changed before or during an operation.

In one exemplary method of use, ball 108 remains in the first spherical end portion 168 of internal cavity 166 when femoral component 102 rotates between 20 degree of flexion (FIG. 11) and 90 degree of flexion (FIG. 12). At 90 degree of flexion, cam 178 of coupling component 106 engages or contacts connecting post 118 of tibial component 104. While femoral component 102 rotates from the 90 degree of flexion to 110 degree of flexion (FIG. 13), femoral component 102 begins to roll back with respect to tibial component 104 when cam 178 engages connecting post 118. For example, femoral component 102 may roll back a distance X with respect to tibial component 104, thereby changing the position of ball 108 relative to internal cavity 166. As femoral component 102 rolls back, coupling component 106, which is fixed to femoral component 102, rolls back as well and displaces internal cavity 166 relative to the tibial component 104. The displacement of internal cavity 166 causes the relocation of ball 108. Specifically, ball 108 gradually relocates from first spherical end portion 168 to second spherical end portion 170. For example, in the 110 degree of flexion, ball 108 is partially positioned in the longitudinal portion 172 of internal cavity 166 between the first and second spherical end portions 168, 170 of internal cavity 166. While femoral component 102 rotates from 110 degree of flexion to 135 degree of flexion, femoral component 102 rolls back further (i.e., a distance Y), displacing internal cavity 166 relative to ball 108. Distance Y is greater than distance X. In the 135 degree of flexion, ball 108 is positioned in the second spherical end portion 170 of internal cavity 166. Although the drawings show the femoral component 102 articulating relative to the tibial component between 20 and 135 degrees of flexion, the femoral component 102 can articulate up to 150 degrees of flexion.

Figure 16:
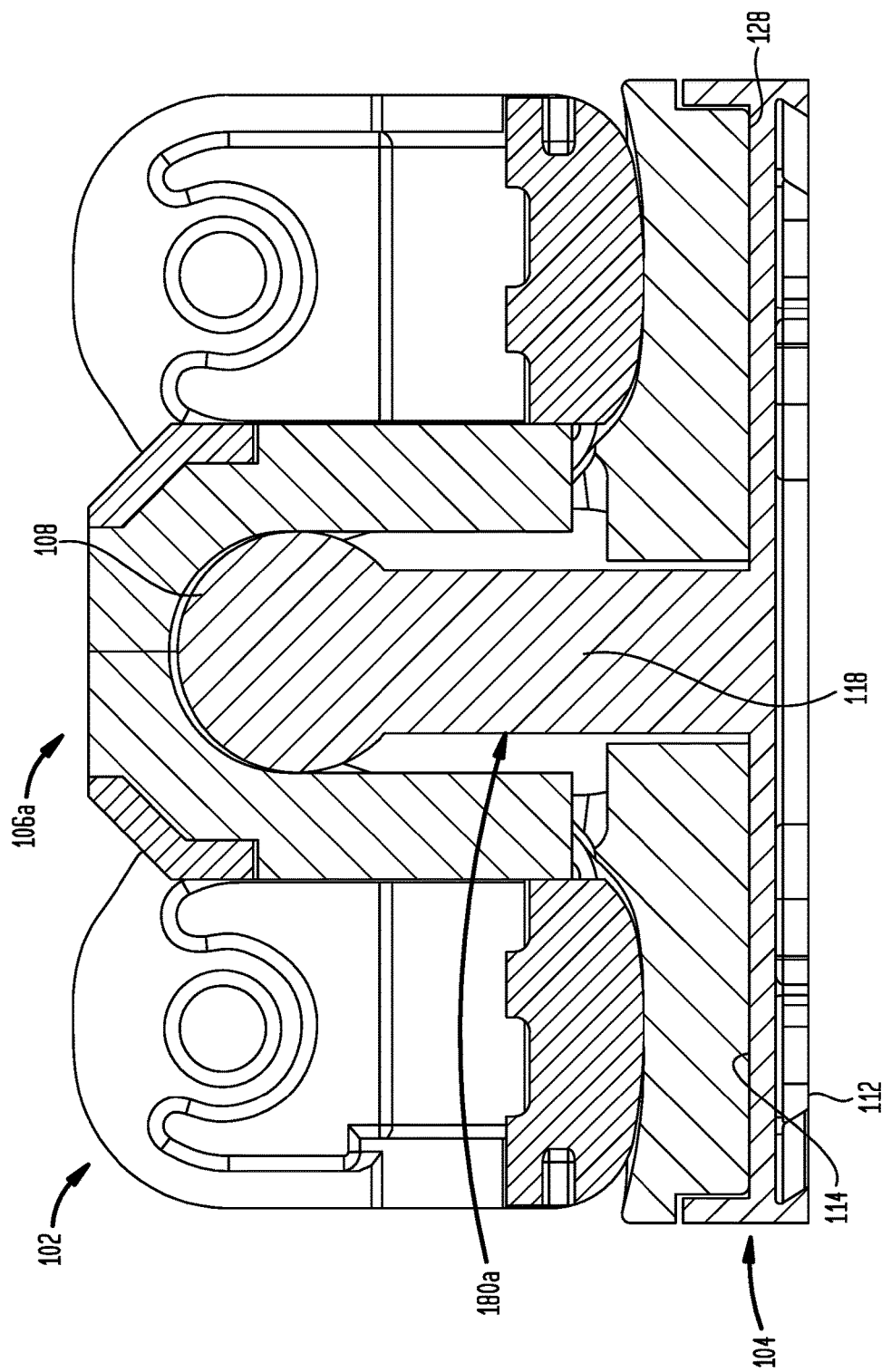
FIG. 16 is a cross-sectional view, taken along a plane parallel to the coronal plane, of another embodiment of the knee prosthesis.

FIG. 16 shows knee prosthesis 100 with an alternate coupling component 106a. Coupling component 106 defines a slot 180a that does not closely fits connecting post 118. In this embodiment, slot 180a may have a diameter substantially similar or equal to the diameter of ball 108. Coupling component 106a does not resist varus or valgus moment.

Which coupling component 106, 106a is selected depends on the level of varus/valgus constraint required for the patient, which in turn is based on the health and function of the collateral ligaments. If a high level of varus/valgus constraint is required, coupling component 106 may be used. (See FIG. 2). In the embodiment of knee prosthesis 100 shown in FIG. 2, varus/valgus moments are counteracted by the close fit between the diameter of ball 108 and spherical cavity (168 or 170) in conjunction with the close fit between the diameter of the connecting post 118 and widths of slot 136 of tibial component 104 and slot 180 of coupling component 106, respectively. A high level of varus/valgus constraint is possible without restricting all other levels of movement, i.e., internal/external rotation, A-P stability and rollback. Conversely, if no varus/valgus constraint is required, coupling component 106a may be used. (See FIG. 16). Coupling component 106a does not resist varus or valgus moment.

Knee prosthesis 100 reduces the A-P laxity (i.e., A-P stability) at important points of flexion (i.e., 0 degree to 60 degree of flexion). In addition, knee prosthesis 100 constrains varus/valgus movement while still allowing internal/external flexion. The amount of varus/valgus constraint depends of the coupling component (106 or 106a), which can be changed by simply swapping out the coupling component instead of replacing the tibial component 104 and femoral component 102. The coupling component (106 or 106a) may be changed before the operation or during the operation. The design of knee prosthesis 100 permits smooth kinematics (flexion/extension, internal/external rotation, rollback) due to placement of ball 108 with respect to the flexion axis. The design of ball 108 and internal cavity 166 of coupling component 106 allows knee prosthesis 100 to undergo a natural motion during articulation. The tibial component 104 (as opposed to ball 108) provides a low friction articular surface capable of transferring compressive loads to the tibia. The small ball 108 and coupling component 106 enables a longer anatomic patella track on the anterior flange.

Figure 17:
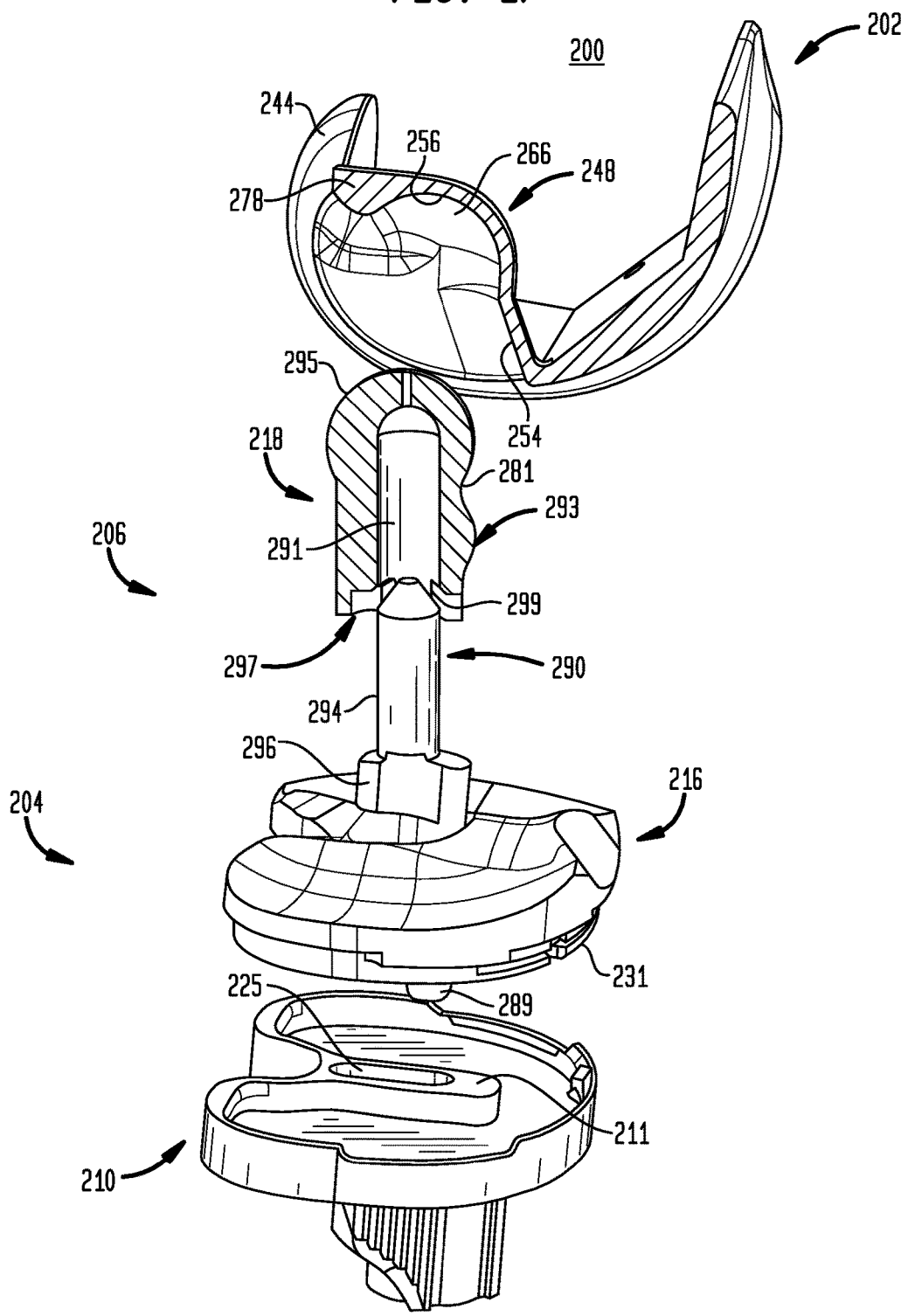
FIG. 17 is a perspective sectional view of a further embodiment of the knee prosthesis with a protrusion on the post anterior surface.

During installation of knee prosthesis 100, the traditional primary cuts can be made on the femur and tibia. Moreover, bone does not need to be removed from the femur to accommodate a pin as required in a traditional hinge design. When a pin is employed, the medial and lateral sides of the bone have to be resected, whereas, in this design, only the intercondylar areas of the bone have to be resected. Also during installation, coupling component 106 or 106a can be inserted and fixed to femoral component 102 by sliding extensions 169 along slot apertures 159 of femoral component. FIG. 17 shows an alternate embodiment of a stabilized knee prosthesis 200 for replacing a natural knee joint. Knee prosthesis 200 includes a femoral component 202, a tibial component 204, and a coupling component 206 movably connecting femoral component 202 to tibial component 204. Femoral component 202 is therefore movably coupled to tibial component 204.

Figure 18:
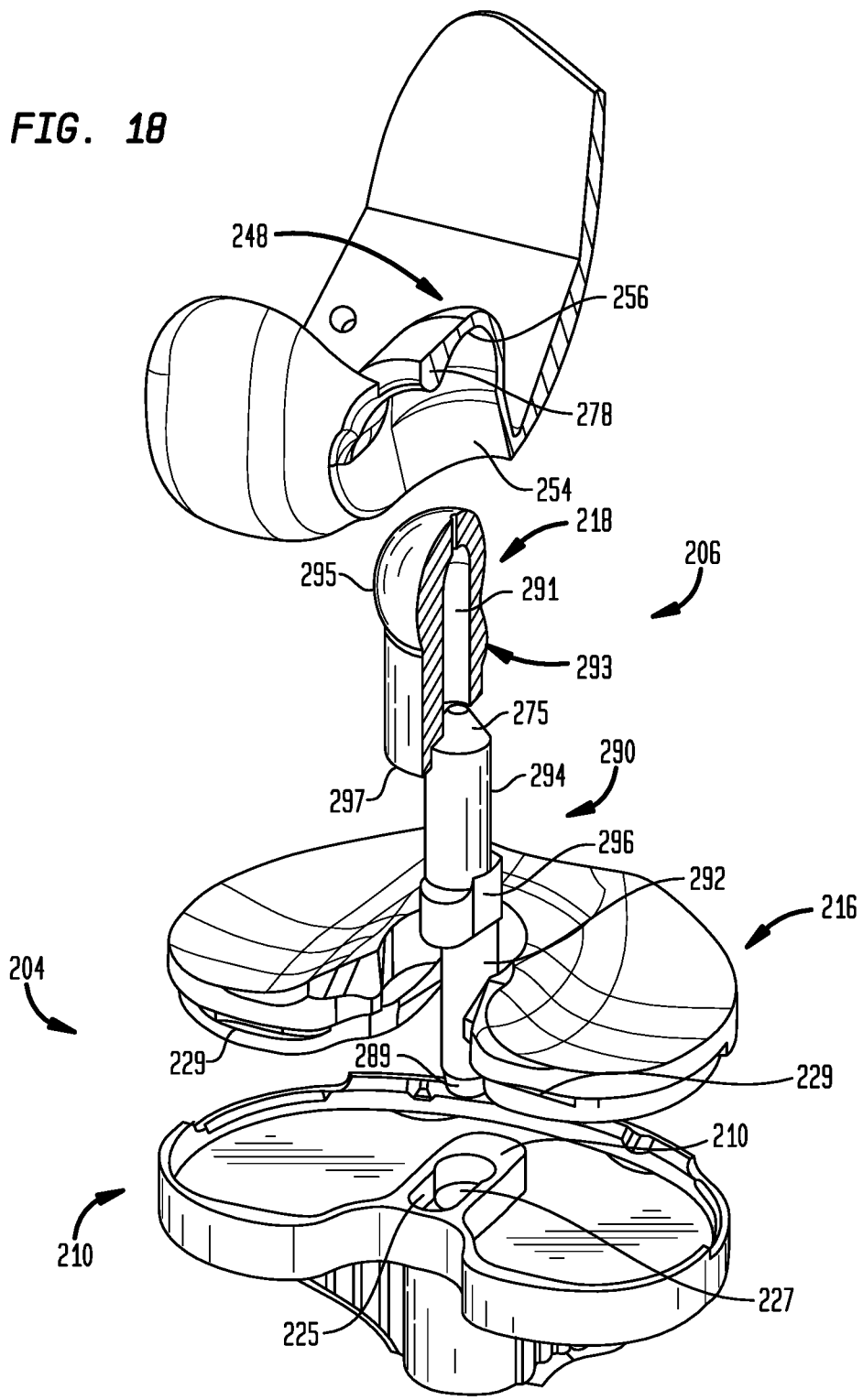
FIG. 18 is another perspective sectional view of the embodiment of the knee prosthesis depicted in FIG. 17.
Figure 19:
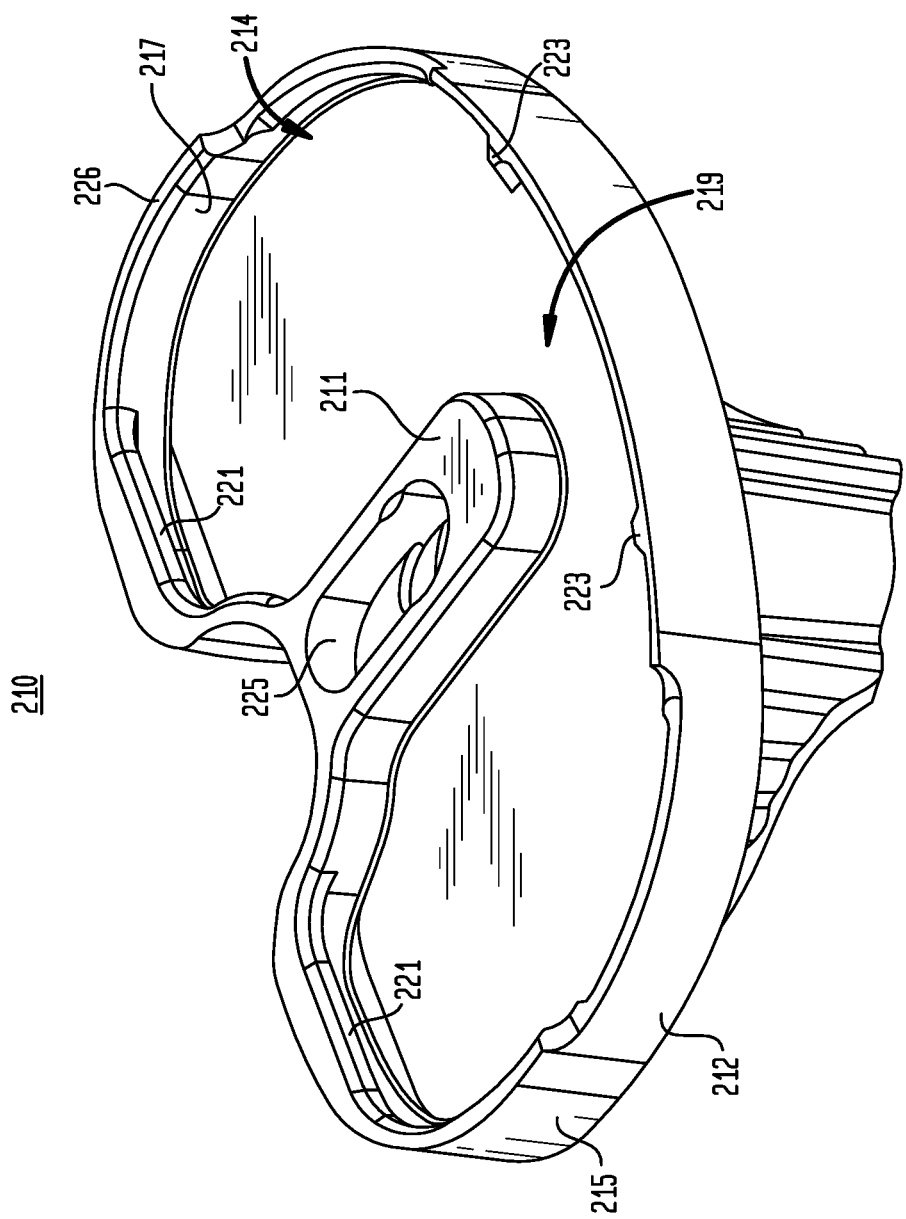
FIG. 19 is a perspective view of a tibial baseplate of the knee prosthesis shown in FIG. 17.
Figure 21:
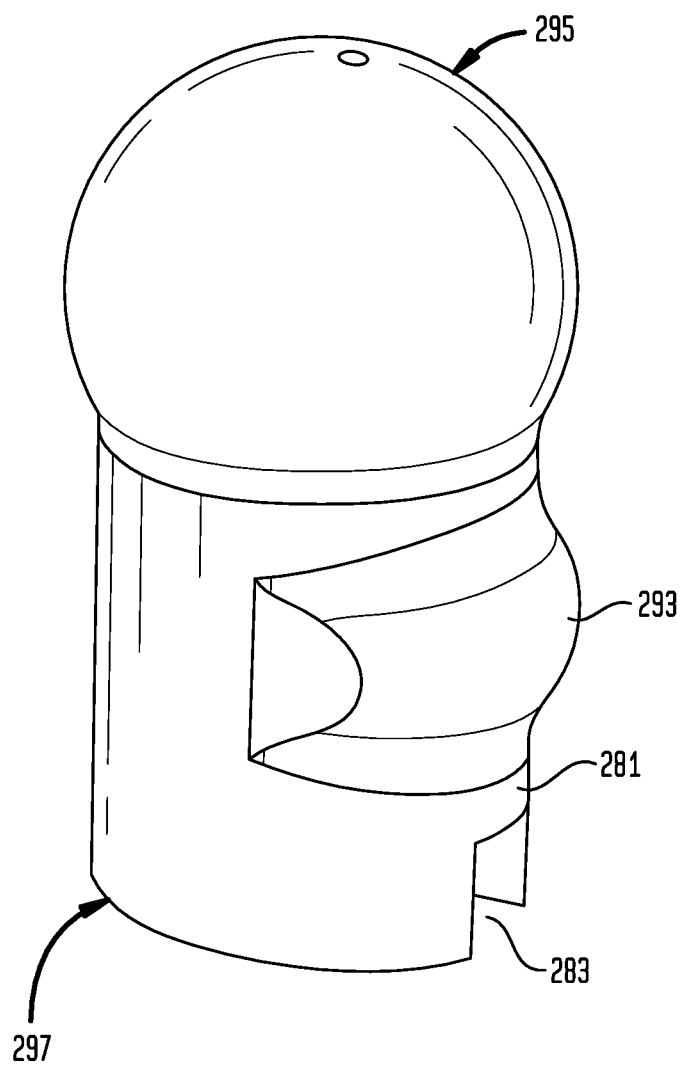
FIG. 21 is a perspective view of a connecting post with a bumper integrally formed therewith.

Tibial component 204 includes a tibial baseplate 210 and a tibial bearing insert or component 216. When tibial component 204 is completely assembled, tibial baseplate 210 supports tibial bearing insert 216 (see FIG. 24). As seen in FIG. 19, tibial baseplate 210 may have a substantially oblong shape matching the proximal tibia and includes an intercondylar support 211 for supporting, among other things, a stabilizing post 218 (see FIG. 21). Support 211 has an opening or cavity 225 dimensioned for receiving at least a portion of a support post 290 (see FIG. 22). Further, support 211 has a bore 227 (see FIG. 18) located within cavity 225. Bore 227 is dimensioned to receive a portion of support post 290, as discussed in further detail below. In addition to support 211, tibial base plate 210 has a first bone contacting bottom portion 212 for engaging the proximal tibia and a second opposite top portion 214 for supporting tibial bearing insert 216 (see FIG. 24). The top portion 214 of tibial baseplate 210 includes a rim or wall 226 enclosing cavity or opening 219. Opening 219 is dimensioned to receive at least a portion of tibial bearing insert 216. Wall 226 has medial and lateral sides 215 and 217, which are oriented in directly opposite relationship with respect to each other and are oriented medially or laterally depending on whether the baseplate 210 is on the left or right tibia. Tibial baseplate 210 further includes extensions 221 and 223 protruding from wall or rim 226. Extensions 221 and 223 facilitate a snap connection between tibial baseplate 210 and tibial bearing insert 216.

Figure 23:
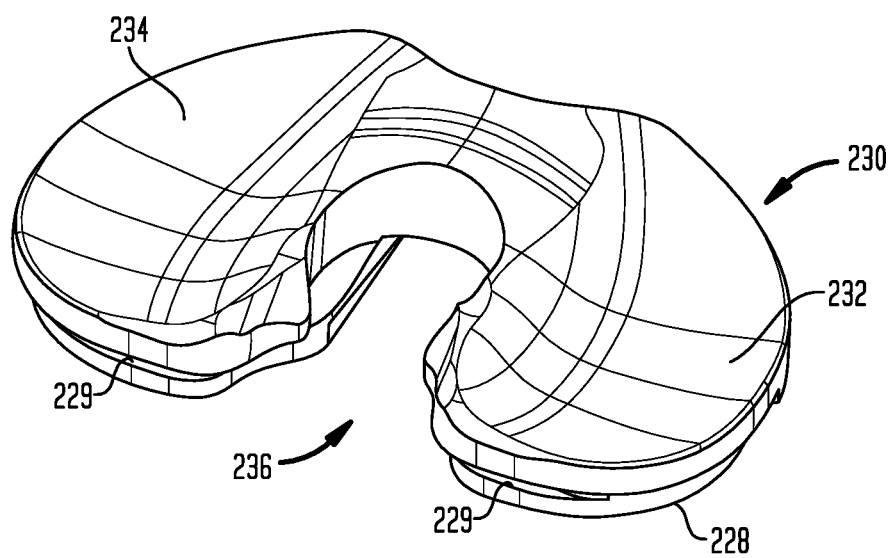
FIG. 23 is a perspective view of a tibial insert of the knee prosthesis of FIG. 17.

With reference to FIG. 23, the tibial bearing insert 216 of tibial component 204 allows articulation of femoral component 202 relative to tibial component 204 and includes a first distally facing side 228 for securely engaging the second proximally facing side 214 of tibial baseplate 210 and a second side 230 for providing a bearing surface for supporting at least a condylar portion of femoral component 202. First side 228 may have posterior recessed grooves or slits 229 for securely receiving extensions 221 of tibial bearing baseplate 210 and anterior recessed grooves or slits 231 (see FIG. 17) for securely receiving extensions 223 of tibial bearing baseplate 210. Second side 230 has a medial condyle track 232 and a lateral condyle track 234. Each condyle track 232, 234 is adapted to receive and support a condyle of femoral component 202. Tibial bearing insert 216 defines a clearance slot 236 between the condylar tracks 232 and 234. Clearance slot 236 is dimensioned for securely receiving stabilizing post 218 (see FIG. 25).

Referring again to FIGS. 17 and 18, coupling component 206 includes a stabilizing post 218 and a support post 290. Support post 290 couples stabilizing post 218 to tibial component 204 and reinforces stabilizing post 218 to resist bending forces developed during flexion. Stabilizing post 218 allows articulation of femoral component 202 relative to tibial component 204 and may be wholly or partly made of polyethylene or any other suitable polymer. Suitable polymers include, but are not limited to, polyether ether ketone (PEEK) and ultra high molecular weight polyethylene (UHMWPE). Moreover, stabilizing post 218 has a rounded end 295, an open end 297, an inner channel 291 dimensioned to receive support post 290, and a bumper or protrusion 293 located on an anterior surface 281. The rounded end 295 of stabilizing post 218 may have a substantially hemispherical or spherical shape. Protrusion 293 is positioned between the rounded end 295 and the open end 297 of stabilizing post 218 closer to the upper surface of bearing insert 216 (increasing bending resistance) and can engage an anterior wall 254 of a housing 248 of femoral component 202 during hyperextension of the knee to minimize edge loading of the post 218 in that region. The open end 297 of stabilizing post 218 has an aperture 299 leading to inner channel 291. Aperture 299 is dimensioned for receiving at least a portion of support post 290. The open end 297 of stabilizing post 218 further has a rectangular notch or opening 283 on its anterior side. Rectangular opening 283 is dimensioned for receiving at least a portion of support post 290, as discussed further below. When support post 290 and stabilizing post 218 are connected to tibial component 204, stabilizing post 218 and support post 290 define an oblique angle relative to the tibial component 204. Stabilizing post 218 may have different sizes and thicknesses. The size of stabilizing post 218 may affect the varus/valgus constraint of the knee prosthesis 200. For example, the varus/valgus constraint of knee prosthesis 200 may be increased by increasing the thickness of the stabilizing post 218.

Figure 22:
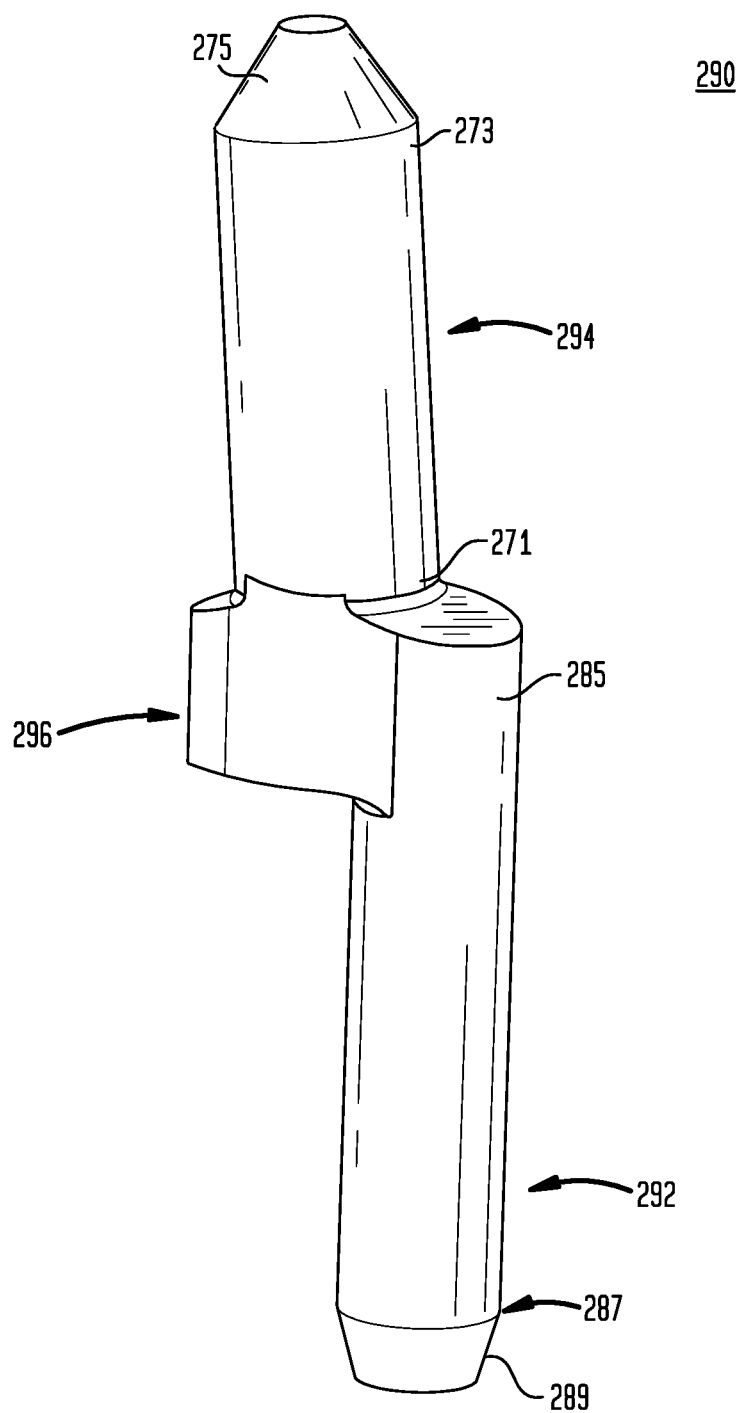
FIG. 22 is a perspective view of a support post for providing support to the connecting post of FIG. 21.

Referring to FIG. 22, the support post 290 of coupling component 206 may be made of any substantially rigid material, such as a suitable metal, and enhances the structural integrity of stabilizing post 218. Suitable metals include, but are not limited to, stainless steel, titanium, titanium alloy, cobalt-chromium-molybdenum alloys (e.g., cobalt-chromium-molybdenum alloy sold under the trademark Vitallium® owned by Stryker Corporation). Support post 290 may have different sizes or heights. The height of support post 290 should be directly proportional to the size of the knee prosthesis 200. For example, larger knee prostheses 200 should include taller support posts 290. In one embodiment, support post 290 includes a first elongated member 292, a second elongated member 294, and a supporting connector 296 attaching first elongated member 292 and second elongated member 294. Support post 290 may be a monolithic structure or a modular structure made of two or more separate pieces or parts. For instance, support post 290 may be formed of three separate or discrete parts, namely the first elongated member 292, the second elongated member 294, and the supporting connector 296. Each of first elongated member 292 and second elongated member 294 may be substantially similar and sized to be received within inner channel 291 of stabilizing post 218. In one embodiment, first elongated member 292 and/or second elongated member 294 may have a substantially cylindrical shape. Regardless of their shape, the first elongated member 292 and/or second elongated member 294 is dimensioned to pass through bore 227 (see FIG. 18) of tibial baseplate 210. First elongated member 292 may have a first end 285 attached to supporting connector 296 and a second end 287 with a tapered region 289. Second elongated member 294 also has a first end 271 attached to supporting connector 296 and a second end 273 with a tapered region 275. Supporting connector 296 may have a substantially elliptical cross-section and is dimensioned to be received within cavity 225 of tibial baseplate 210. When knee prosthesis 200 is completely assembled, supporting connector 296 is located within cavity 225 of tibial baseplate 210, one elongated member 292 or 294 is positioned along bore 227, and another elongated member 292 or 294 extends through inner channel 291 of stabilizing post 218.

Figure 20:
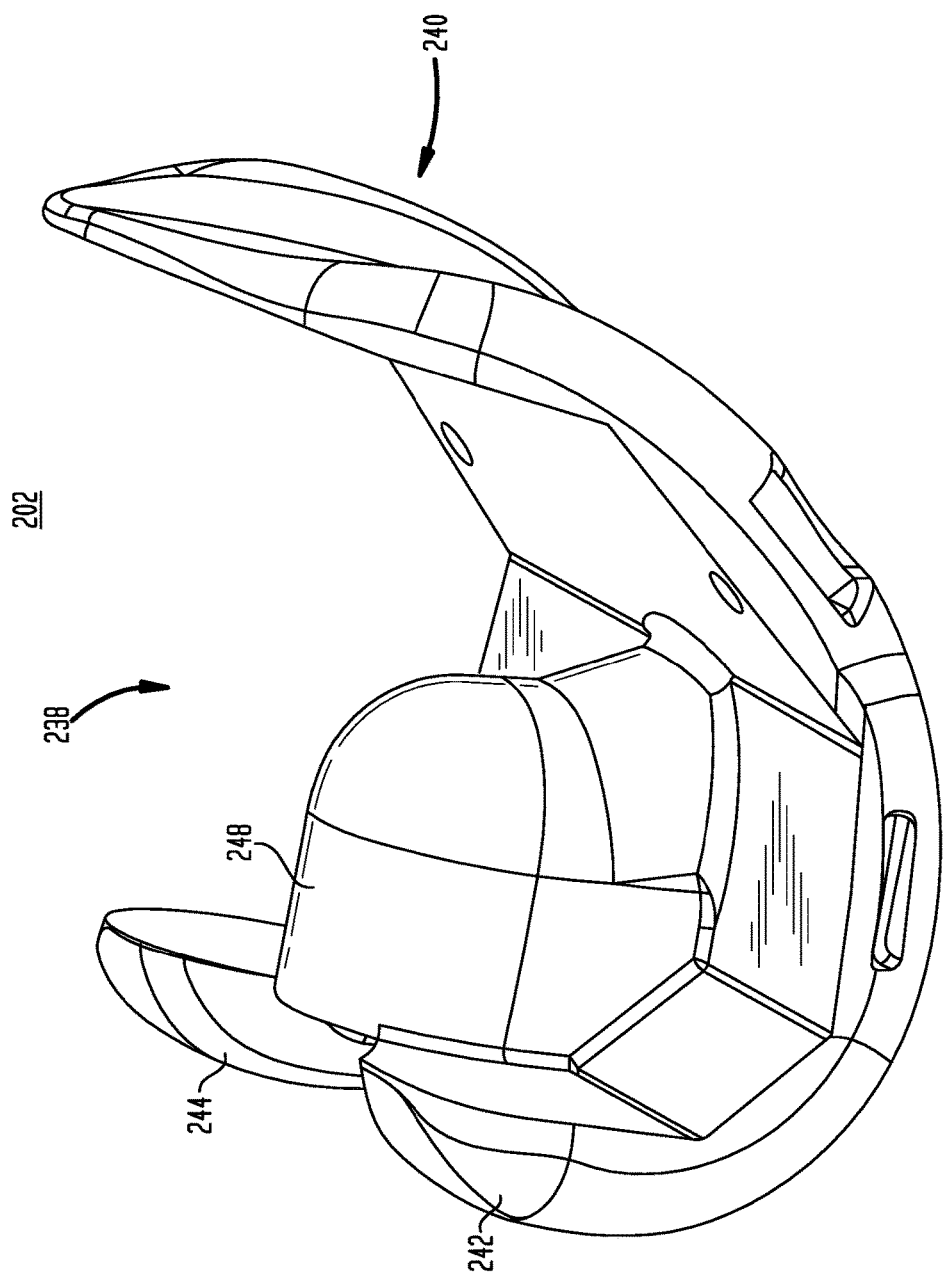
FIG. 20 is a perspective view of a femoral component of the knee prosthesis of FIG. 17.

With reference to FIG. 20, femoral component 202 has a first or proximal side 238 for securely engaging a distal femur and a second or distal side 240 forming a condylar bearing surface. The second side 240 of femoral component 202 includes a first or medial condyle 242 and a second or lateral condyle 244. Each of first condyle track 232 and second condyle track 234 of the tibial component 204 are configured to receive first and second condyles 242, 244, respectively. The second side 240 of femoral component 202 further includes a patella track (not shown) between first and second condyles 242, 244 and is adapted to receive a patellar implant (not shown). The first side 238 of femoral component 202 includes a housing 248 between the first and second condyles 242, 244. Housing 248 may be monolithically formed with femoral component 202 and includes an anterior wall 254 and a proximal wall 256 as seen in FIG. 17. The proximal wall 256 of housing 248 includes a cam 278 configured to engage stabilizing post 218 upon articulation of femoral component 202 relative to tibial component 204. Housing 248 forms an internal pocket or cavity 266 dimensioned to receive the rounded end 295 of stabilizing post 218. Therefore, at least a portion of cavity 266 may have a substantially spherical shape.

Figure 24:
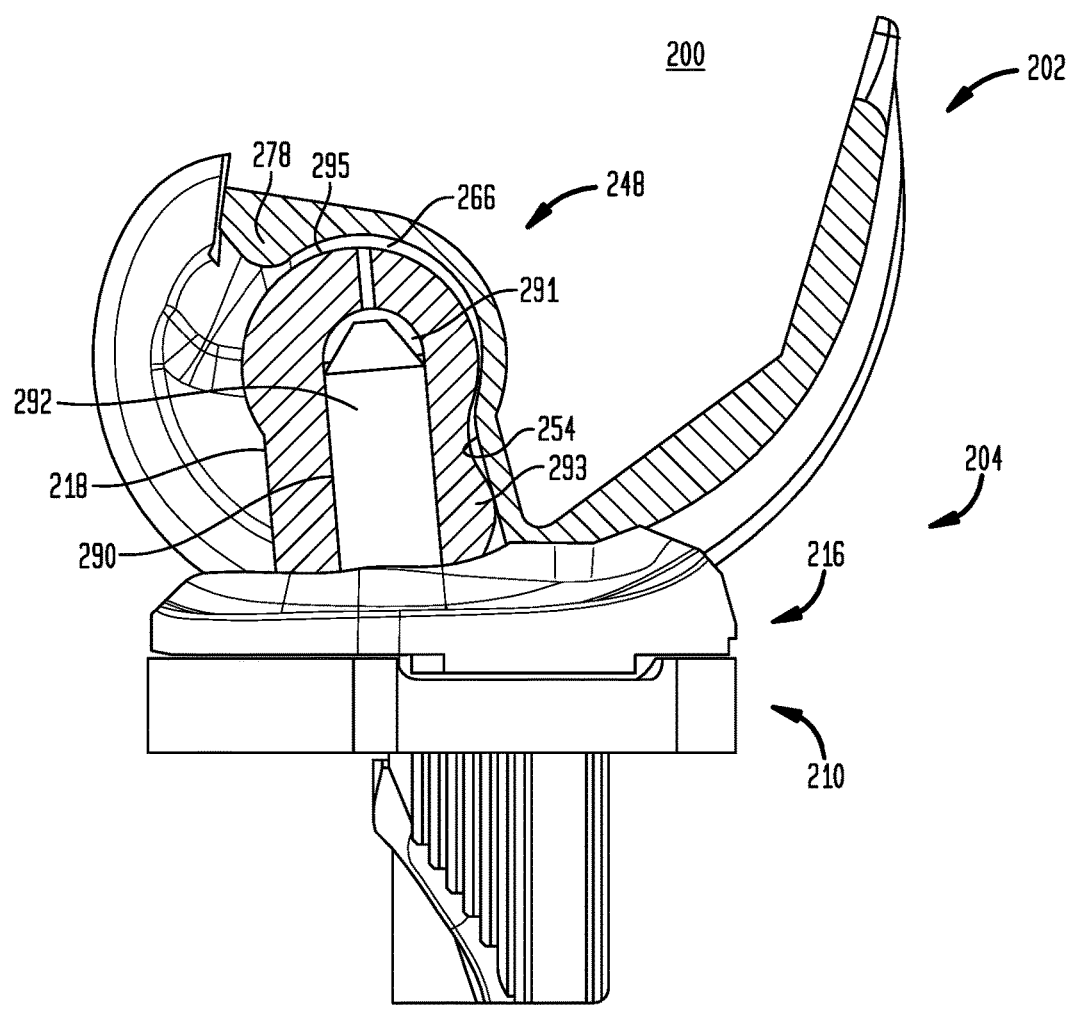
FIG. 24 is a perspective sectional view of a knee prosthesis of FIG. 17 in hyperextension, showing the bumper of the connecting post engaging a portion of the femoral component.

With reference to FIG. 24, a completely assembled knee prosthesis 200 may be employed to replace a knee joint as described above with respect to the knee prosthesis 100. To assemble knee prosthesis 200, a user or manufacturer may first attach tibial bearing insert 216 to tibial baseplate 210. Tibial bearing insert 216 can be locked to tibial baseplate 210 by inserting extensions 221 and 223 in slits 229 and 231, respectively. Support post 290 is then introduced through clearance slot 236 of tibial bearing insert 216 until support connector 296 is securely positioned in cavity 225 of tibial baseplate 210. At this point, one elongated member (292 or 294) of support post 290 is located in bore 227 of tibial baseplate 210. The other elongated member (292 or 294) of support post 290 extends away from tibial component 204. Stabilizing post 218 is placed over the exposed elongated member (292 or 294) of support post 290 such that said elongated member is positioned in inner channel 291. Alternatively, stabilizing post 218 may be placed over support post 290 before attaching support post 290 to tibial bearing insert 216. In addition, the protrusion 293 of stabilizing post 218 should face the anterior portion of tibial component 204, as seen in FIG. 24. Stabilizing post 218 and support post 290 may either be assembled at the time of surgery or preassembled at the factory. Then, femoral component 202 is placed over the stabilizing post 218 such that the rounded end 295 of stabilizing post 218 is situated within the cavity 266 of housing 248.

After knee prosthesis 200 has been assembled, femoral component 202 can articulate relative to stabilizing post 218 about a wide range of flexion degrees. As seen in FIG. 24, protrusion 293 contacts the anterior wall 254 of housing 248 during hyperextension of the knee, thereby minimizing edge loading of stabilizing post 218 in that contact region.

Figure 25:
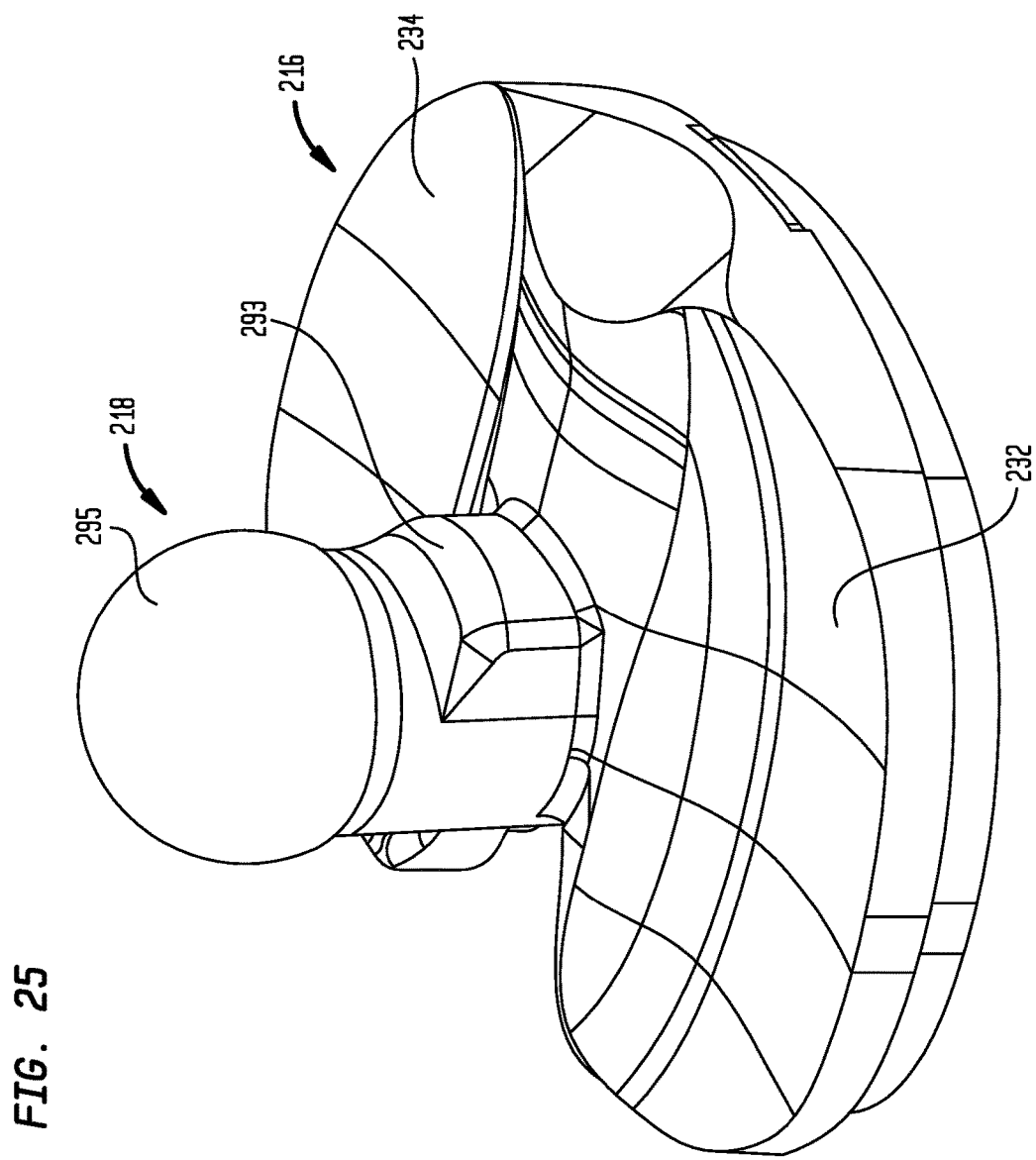
FIG. 25 is a perspective view of a tibial insert with an integrally formed connecting post.
Figure 26:
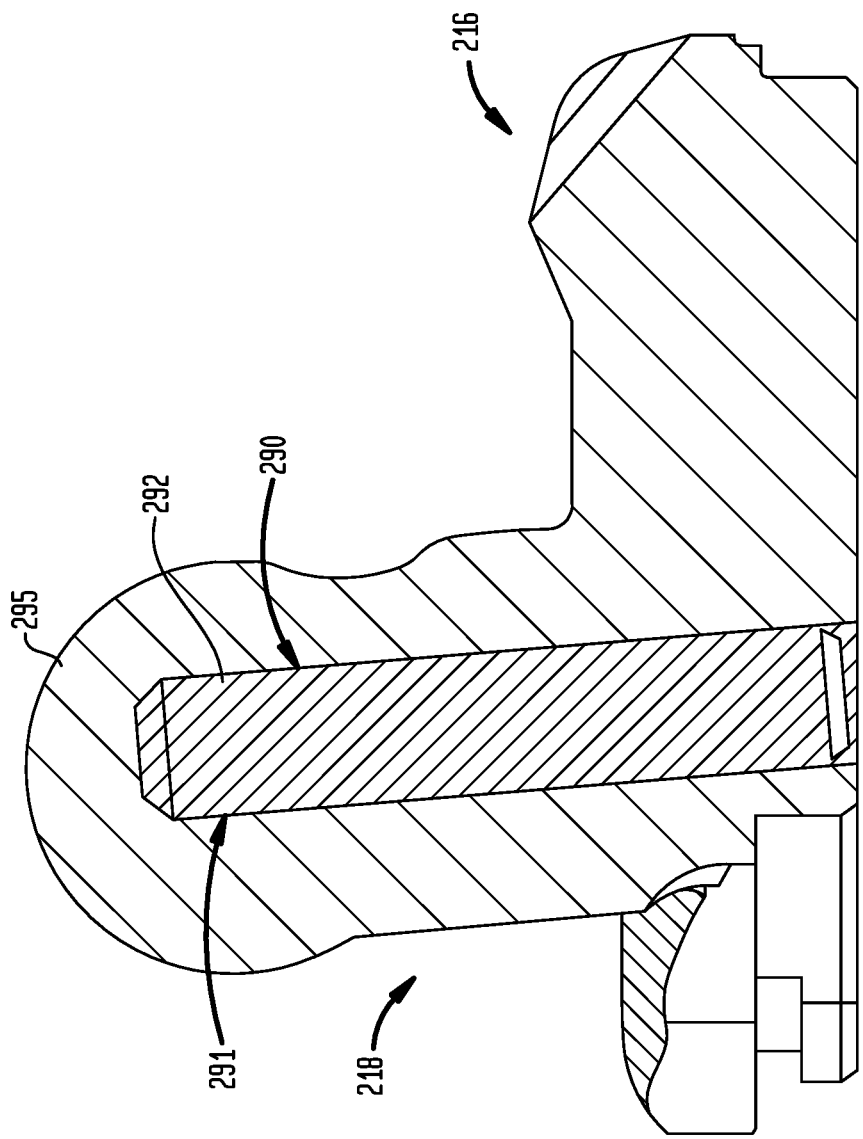
FIG. 26 is a side sectional view of the tibial insert of FIG. 25.

FIGS. 25 and 26 show an alternate embodiment of knee prosthesis 200, wherein tibial bearing insert 216 and stabilizing post 218 are made from a single piece. In other words, stabilizing post 218 is monolithically or integrally formed with tibial bearing insert 216. In this embodiment, support post 218 includes only one elongated member 292 and does not include a support connector. Elongated member 292 is dimensioned to be received within inner channel 291 of stabilizing post 218 and enhances the structural integrity of stabilizing post 218. In a further embodiment, stabilizing post 218 may be integrally or monolithically formed with tibial baseplate 210.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of varying an angular constraint of a knee prosthesis comprising:
    inserting a portion of a first stabilizing post coupled to a tibial baseplate within a housing of a femoral component, the first stabilizing post having a thickness and an outer surface with a protrusion extending outwards from the outer surface, the first stabilizing post movably interconnecting the femoral component to the tibial baseplate, the protrusion being configured to engage a wall of the housing during hyperextension of a knee, the tibial baseplate including a tibial insert having an articular surface configured to articulate with condylar surfaces of the femoral component,
    wherein the first stabilizing post includes a support post at least partially positioned within the first stabilizing post;
    allowing the femoral component to articulate with respect to the tibial baseplate, the femoral component having a first angular constraint relative to the tibial baseplate based on the thickness of the first stabilizing post;
    exchanging the first stabilizing post for a second stabilizing post of a different thickness than the first stabilizing post without removing the tibial insert, wherein exchanging includes:
        removing the first stabilizing post from the support post, and
        coupling the second stabilizing post to the support post;
    inserting a portion of the second stabilizing post within the housing of the femoral component; and
    allowing the femoral component to articulate with respect to the tibial baseplate, the femoral component having a second angular constraint relative to the tibial baseplate based on the thickness of the second stabilizing post.

2. The method of claim 1, wherein the housing of the femoral component includes an enclosed internal cavity adapted to receive a portion of the first stabilizing post.

3. The method of claim 1, wherein the first stabilizing post includes a rounded end positioned within the housing of the femoral component.

4. The method of claim 1, wherein the support post includes a first elongated member positioned inside the first stabilizing post and a second elongated member positioned within the tibial component.

5. The method of claim 1, wherein the first stabilizing post has an inner bore configured to receive the support post.

6. The method of claim 1, wherein the wall is an anterior wall of the housing.

7. The method of claim 1, wherein the angular constraint is a varus-valgus constraint.

8. A method of determining a preferred angular constraint of a knee prosthesis comprising:
    inserting a portion of a first stabilizing post having a first thickness coupled to a tibial baseplate within a housing of a femoral component, the first stabilizing post movably interconnecting the femoral component to the tibial baseplate;
    allowing the femoral component to articulate with respect to the tibial baseplate to determine a first angular constraint of the knee prosthesis;
    removing the first stabilizing post from the tibial baseplate and from a support post at least partially positioned within the first stabilizing post;
    coupling a second stabilizing post having a second thickness different than the first thickness to the tibial baseplate by inserting the support post at least partially into the second stabilizing post;
    inserting a portion of the second stabilizing post within the housing of the femoral component, the second stabilizing post movably interconnecting the femoral component to the tibial baseplate; and
    allowing the femoral component to articulate with respect to the tibial baseplate to determine a second angular constraint of the knee prosthesis, the second angular constraint being greater than the first angular constraint,
    wherein the preferred angular constraint is chosen from the first and second determined angular constraints, wherein each of the first and second stabilizing posts have an outer surface with a protrusion extending outwards from the outer surface, the protrusion being configured to engage a wall of the housing during hyperextension of a knee.

9. The method of claim 8, wherein a tibial insert is coupled to the tibial baseplate and the allowing steps include allowing the femoral component to contact and articulate with respect to the tibial insert.

10. The method of claim 9, wherein the first stabilizing post is removed from the tibial baseplate without removing the tibial insert.

11. The method of claim 8, wherein the housing of the femoral component includes an enclosed internal cavity adapted to receive a portion of and second stabilizing posts.

12. The method of claim 8, wherein the first and second stabilizing posts each include a rounded end positioned within the housing of the femoral component.

13. The method of claim 8, wherein each of the first and second stabilizing posts have an inner bore configured to receive the support post.

14. The method of claim 8, wherein the wall is an anterior wall of the housing.

15. The method of claim 8, wherein the angular constraint is a varus-valgus constraint.

* * * * *